United States Patent
Li et al.

(10) Patent No.: US 8,299,106 B2
(45) Date of Patent: Oct. 30, 2012

(54) COMPOSITIONS OF KINASE INHIBITORS AND THEIR USE FOR TREATMENT OF CANCER AND OTHER DISEASES RELATED TO KINASES

(75) Inventors: Chiang Jia Li, Cambridge, MA (US); Ji-Feng Liu, Winchester, MA (US); Youzhi Li, Westwood, MA (US); Wei Li, Wayland, MA (US); Harry Rogoff, Wrentham, MA (US)

(73) Assignee: Boston Biomedical, Inc., Norwood, MA (US)

( * ) Notice: Subject to any disclaimer, the term of this patent is extended or adjusted under 35 U.S.C. 154(b) by 0 days.

(21) Appl. No.: 12/676,869

(22) PCT Filed: Sep. 5, 2008

(86) PCT No.: PCT/US2008/075418
§ 371 (c)(1),
(2), (4) Date: Aug. 2, 2010

(87) PCT Pub. No.: WO2009/033033
PCT Pub. Date: Mar. 12, 2009

(65) Prior Publication Data
US 2010/0285006 A1 Nov. 11, 2010

Related U.S. Application Data

(60) Provisional application No. 60/970,410, filed on Sep. 6, 2007, provisional application No. 61/013,389, filed on Dec. 13, 2007, provisional application No. 61/074,295, filed on Jun. 20, 2008.

(51) Int. Cl.
*A01N 43/78* (2006.01)
*A61K 31/425* (2006.01)

(52) U.S. Cl. .................................... 514/365

(58) Field of Classification Search ............... 514/365
See application file for complete search history.

(56) References Cited

U.S. PATENT DOCUMENTS

| 6,268,391 B1 * | 7/2001 | Dickerson et al. | 514/418 |
|---|---|---|---|
| 2004/0043388 A1 | 3/2004 | Come et al. | |
| 2005/0032871 A1 | 2/2005 | Tang et al. | |

FOREIGN PATENT DOCUMENTS

| WO | WO-9807695 A1 | 2/1998 |
|---|---|---|
| WO | WO 99/10325 | 3/1999 |
| WO | WO 99/15524 | 4/1999 |
| WO | WO-0160814 A2 | 8/2001 |
| WO | WO-0164681 A2 | 9/2001 |
| WO | WO-0194312 A2 | 12/2001 |
| WO | WO-02081466 A1 | 10/2002 |
| WO | WO-03051838 A2 | 6/2003 |
| WO | WO-2005040116 A2 | 5/2005 |
| WO | WO-2007085188 A1 | 8/2007 |

OTHER PUBLICATIONS

K. Lackey, et al. "The Discovery of Potent cRaf1 Kinase Inhibitors," Bioorganic & Medicinal Chem Letters 10 (2000) 223-26.

* cited by examiner

*Primary Examiner* — Gina C Yu
*Assistant Examiner* — Michael B Pallay
(74) *Attorney, Agent, or Firm* — Mintz Levin Cohn Ferris Glovsky and Popeo, P.C.; Ivor R. Elrifi; Jennifer A. Karnakis, Esq.

(57) ABSTRACT

The present invention relates to novel thiazole-substituted indolin-2-ones as inhibitors of CSCPK and related kinases; to methods of inhibiting cancer stem cells by using a kinase inhibitor; to pharmaceutical compositions containing such compounds; and to methods of using such compounds in the treatment of a protein kinase related disorder in a mammal; and to processes of making such compounds and intermediates thereof.

6 Claims, 12 Drawing Sheets

Control TKI

Compound 10-2

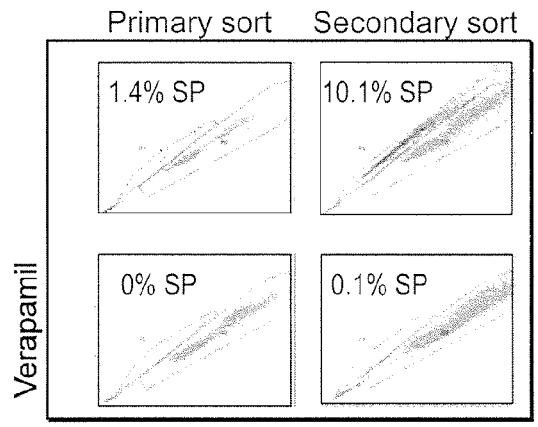
FIG. 4A
| | | IC$_{50}$ | SP phenotype |
|---|---|---|---|
| Doxorubicin | NSP | 2.7 nM | - |
| | SP | 33.6 nM | 12.5-fold more resistant |
| 10-2 | NSP | 430 nM | - |
| | SP | 220 nM | 2-fold more sensitive |
FIG. 4B
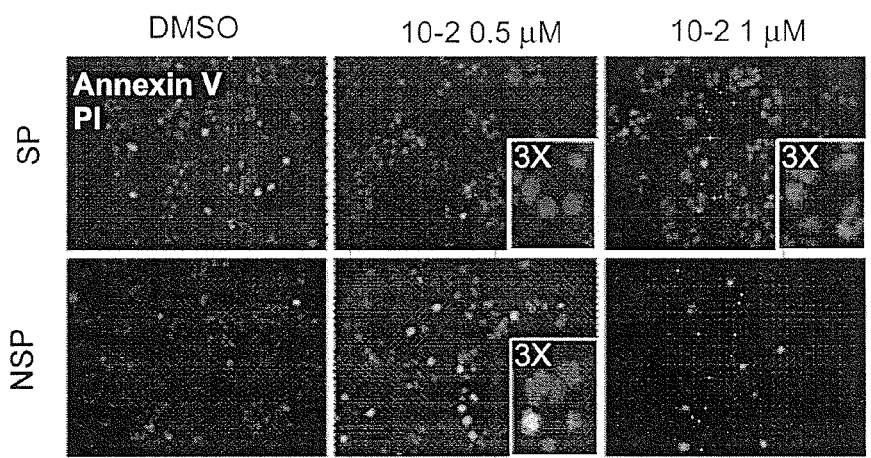
FIG. 4C

COMPOSITIONS OF KINASE INHIBITORS AND THEIR USE FOR TREATMENT OF CANCER AND OTHER DISEASES RELATED TO KINASES

CROSS REFERENCE TO RELATED APPLICATIONS

This application claims the benefit of priority under 35 U.S.C. §119(e) to U.S. Patent Application Ser. Nos. 60/970,410 filed Sep. 6, 2007, 61/013,389 filed Dec. 13, 2007, and 61/074,295 filed Jun. 20, 2008, each of which is hereby incorporated by reference in its entirety.

FIELD OF THE INVENTION

The present invention relates to composition and methods of use of novel thiazole-substituted indolin-2-ones as inhibitors of cancer stem cells as well as cancer stem cell pathway kinase (Cancer Stem Cell Pathway Kinase—CSCPK) and other related kinases; to pharmaceutical compositions containing such compounds; and to methods of using such compounds in the treatment of a protein kinase related disorder in a mammal; and to processes of making such compounds and intermediates thereof.

BACKGROUND OF THE INVENTION

Despite decades of efforts in the cancer therapies, cancer remains a huge public health burden. Surgery and radiotherapy are quite successful in treating primary tumors. However, once a cancer has disseminated to distant sites, chemotherapy is often required to treat the disease. Cytotoxic agents have played a critical role in modern cancer therapy. However, they usually induce substantial toxicity in normal tissues. The principle for treatment of cancer has changed. Cytotoxic drugs are losing their dominance in the chemotherapy world and targeted therapies are being developed with the aim of more specifically targeting cancer cells. Targeted cancer therapies are a relatively new class of agents with selectivity for targets implicated in tumor growth. They have demonstrated impressive efficacy with much less toxicity than cytotoxic agents.

Protein kinases are a family of enzymes that regulate a wide variety of cellular processes, including cell growth, cell profileration, cell differentiation and metabolism. The protein kinases communicate cell growth signals through sequential chemical modification of pathway partners. Therefore, pharmacologic inhibition of any kinase on a given signal transduction cascade would theoretically block communication along the entire pathway. In addition, it is known that protein kinases play a role in disease states and disorders, for example, kinase mutation mutation and/or overexpression are frequently characterized in cancers, resulting in hyperactivated activity that often correlates with uncontrolled cell growth. For that reason, protein kinases represent potential targets for therapeutic inhibition. [1]. Cancer Stem Cells (CSC) is a subpopulation of cells within a variety of tumor types with a tumorigenic potential that is lacking in the rest of the cells within these tumors. There is mounting evidence that such cells exist in almost all tumor types. CSC give rise to the differentiated cells that form the bulk of the tumor mass and phenotypically characterize the disease. Cancer stem cells have been demonstrated to be fundamentally responsible for carcinogenesis, cancer metastasis, and cancer reoccurrence. In many tumors, CSC and their differentiated progeny appear to have markedly different biologic characteristics. Conventional therapies that target mature tumor cells may lead to clinical improvement, but are unlikely to be curative unless CSCs are also targeted. Relevant targets unique to the rare cancer stem cells may be missed if clinical activity is judged solely by criteria that reflect the effects of treatment on the bulk of the cancer.

We have recently shown that the compounds in this invention inhibit kinases and kill cancer stem cells, demonstrating that kinases are important targets for killing or inhibiting cancer stem cells. These kinases important for CSCs are collectively referred to CSCPK hereafter. Our results provide a method of targeting cancer stem cells with CSCPK inhibitors.

PDGFRα is a receptor tyrosine kinase (RTK) that is activated after binding to its ligand, PDGF, which contributes to cell proliferation, angiogenesis, and apoptosis. It belongs to class III receptor tyrosine kinase family and are related to the CFS-1 receptor/c-fms and the stem cell growth factor/c-kit proto-oncogene family. PDGFRα pathway is active in early fetal development and reactivated in many cancers, such as hepatocellular cancer (HCC), head and neck cancer, brain tumors, gastrointestinal tumors, skin cancer, prostate cancer, ovarian cancer, breast cancer, sarcoma, and leukemia [2-15]. In addition, PDGFRα activation has recently been shown to play a key role in bone metastasis of prostate cancer [16, 17]. Furthermore, PDGFRα-p70S6K pathway has been shown to be essential for angiogenesis in vivo [18]. Specifically targeting PDGFRα using monoclonal antibody has been shown to lead to significant reduction in tumor cell proliferation and survival while being a relatively non-toxic treatment [11]. Therefore, PDGFRα represents a target for developing targeted chemotherapy against broad spectrum of cancers with less toxicity.

Other than cancer, it has been well demonstrated that chromosomal rearrangments activate PDGFRα by fusion to FIP1L1, causing idiopathic hypereosinophilic syndrome [5]. In addition, activation of PDGFRα by promoter polymorphisms has linked to neural tube defects including spina bifida, which has been verified by mouse mutant model [19]. PDGFRα activation has also been linked with fibrosis [20-23]. For that reason, PDGFRα represents a potential target for anti-fibrotic therapy.

SUMMARY

In one aspect, the present invention provides a compound of formula I,

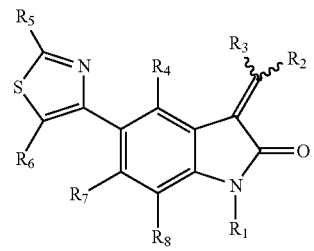

or an enantiomer, diastereomer, tautomer, or pharmaceutically acceptable salt or solvate thereof, wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_aC(=O)NR_bR_c$, $NR_aS(=O)_2NR_bR_c$, $NR_aP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl;

$R_6$ is hydrogen, halogen, cyano, nitro, $CF_3$, $OCF_3$, alkyl or substituted alkyl, heterocycle or substituted heterocycle, aryl or substituted aryl, or $OR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In one aspect, the present invention provides a compound of formula II, $R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_aC(=O)NR_bR_c$, $NR_aS(=O)_2NR_bR_c$, $NR_aP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In yet another aspect, the invention provides a compound of formula III,

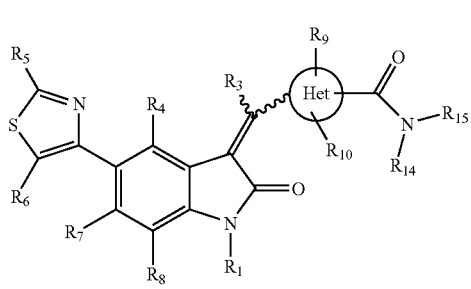

(II)

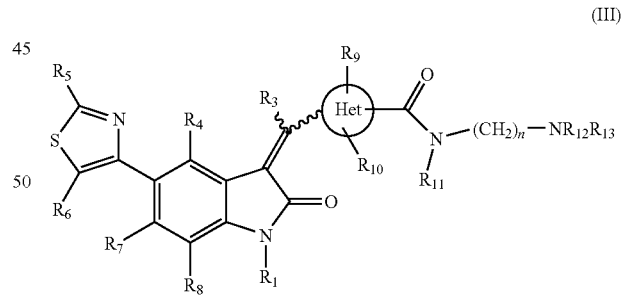

(III)

or an enantiomer, diastereomer, tautomer, or pharmaceutically acceptable salt or solvate thereof, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

or an enantiomer, diastereomer, tautomer, or pharmaceutically acceptable salt or solvate thereof, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{11}$ is hydrogen or $C_{1-4}$ alkyl;

$R_{12}$ and $R_{13}$ are independently hydrogen, alkyl or substituted alkyl, cycloalkyl or substituted cycloalkyl, heterocycle or substituted heterocycle, or aryl or substituted aryl, or said $R_{12}$ and $R_{13}$ together with the N to which they are bonded optionally form a heterocycle or substituted heterocycle;

n is an integer selected from 2, 3, 4, 5 and 6;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In yet another aspect, the invention provides a compound of formula IV,

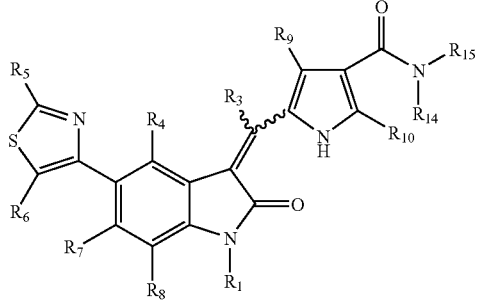

(IV)

or an enantiomer, diastereomer, tautomer, or pharmaceutically acceptable salt or solvate thereof, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In yet another aspect, the invention provides a compound of formula V,

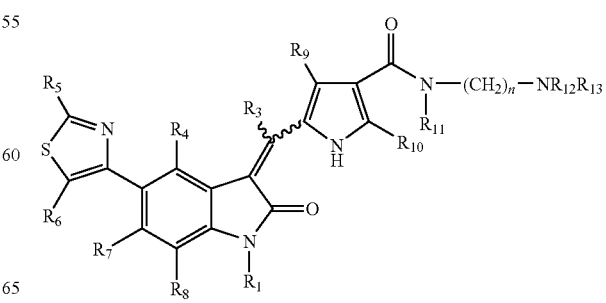

(V)

or an enantiomer, diastereomer, tautomer, or pharmaceutically acceptable salt or solvate thereof, wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_a$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is substituted alkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{11}$ is hydrogen or $C_{1-4}$ alkyl;

$R_{12}$ and $R_{13}$ are independently hydrogen, alkyl or substituted alkyl, cycloalkyl or substituted cycloalkyl, heterocycle or substituted heterocycle, or aryl or substituted aryl, or said $R_{12}$ and $R_{13}$ together with the N to which they are bonded optionally form a heterocycle or substituted heterocycle;

n is an integer selected from 2, 3, 4, 5 and 6;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In a further aspect, the present invention provides a pharmaceutical composition comprising a compound or a pharmaceutically-acceptable salt thereof as described hereinabove and a pharmaceutically-acceptable excipient, carrier, or diluent. In certain embodiments, the pharmaceutical composition further comprises at least one other anti-cancer therapy. In some cases, the at least one other anti-cancer therapy includes radiotherapy (XRT), cytotoxic agents, targeted agents, or adjunctive agents. Non-limiting examples include gemcitabine, erlotinib, Taxol/taxotere, platinum (carboplatin and cisplatin), 5-FU, adriamycin, sorafenib, imatinib, avastin, erbitux, or herceptin.

In one aspect, the present invention provides a method of treating cancers in a mammal, comprising administering to the mammal in need thereof a therapeutically effective amount of a pharmaceutical composition as described hereinabove.

In a further aspect, the present invention provides a method of treating cancers in a mammal, comprising administering to the mammal in need thereof a therapeutically effective amount of a pharmaceutical composition as described hereinabove, to inhibit CSCPKs.

In another aspect, the present invention provides a method of inhibiting/reducing/diminishing cancer stem cell survival and/or proliferation in a mammal by inhibiting or decreasing unwanted activity of CSCPKs in the mammal.

In a further aspect, the present invention provides a method of inhibiting/reducing/diminishing cancer stem cell survival and/or proliferation in a mammal, comprising administering to the mammal in need thereof a therapeutically effective amount of a pharmaceutical composition as described hereinabove.

In another aspect, the present invention provides a method of treating a protein kinase related disorder in a mammal, comprising administering to the mammal in need thereof a therapeutically effective amount of a pharmaceutical composition as described hereinabove.

In another aspect, the present invention provides a method of modulating the catalytic activity of a protein kinase, comprising contacting said protein kinase with a compound or a pharmaceutically-acceptable salt thereof as described hereinabove.

In yet another aspect, the present invention provides a process of making a compound or a pharmaceutically-acceptable salt thereof as described hereinabove and intermediates thereof.

BRIEF DESCRIPTION OF THE FIGURES

FIG. 4A shows the identification of the cancer stem cell enriched Hoechst Side Population (SP).

FIG. 4B shows that compound 10-2 is more potent to the cancer stem cell enriched Hoechst SP.

FIG. 4C shows that compound 10-2 kills Hoechst side population cells by apoptosis.

DETAILED DESCRIPTION

A. Definitions

Figure 1:
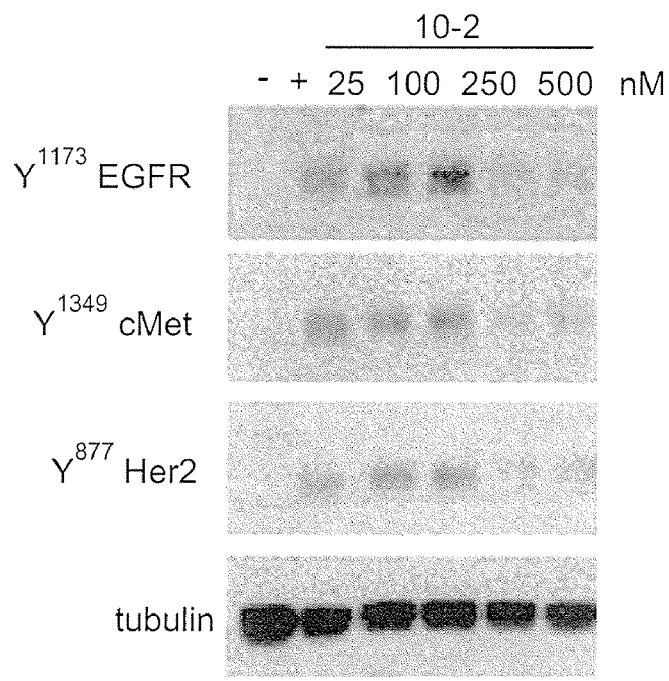
FIG. 1 shows that compound 10-2 blocks activation of EGFR, c-Met and Her2 in a cell assay.

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle or substituted heterocycle; and $R_e$ is alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substitutents can themselves be optionally substituted.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substitutents can themselves be optionally substituted.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. The exemplary substituents can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one or more substituents, preferably 1 to 4 substituents, at any available point of attachment. Exemplary substituents include but are not limited to nitro, cyano, alkyl or substituted alkyl, as well as those groups recited above as exemplary alkyl substituents. The exemplary substitutents can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. The exemplary substitutents can themselves be optionally substituted. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. The exemplary substitutents can themselves be optionally substituted. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The terms "halogen" or "halo" refer to chlorine, bromine, fluorine or iodine.

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents. The exemplary substitutents can themselves be optionally substituted.

The term "heating" includes, but not limited to, conventional heating (e.g., electric heating, steam heating, gas heating, etc.) as well as microwave heating.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-1-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the compounds of the invention are also contemplated herein. Solvates of the compounds of the present invention include, for example, hydrates.

Compounds of the present invention, and salts thereof, may exist in their tautomeric form (for example, as an amide or imino ether). All such tautomeric forms are contemplated herein as part of the present invention.

All stereoisomers of the compounds of the present invention (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 95% ("substantially pure" compound I), which is then used or formulated as described herein. In certain embodiments, the compounds of the present invention are more than 99% pure.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

B. Compounds

In one aspect, the present invention provides a compound of formula I,

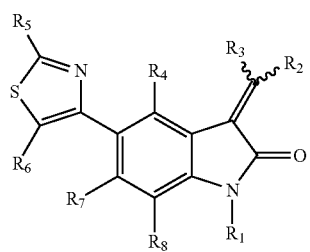

(I)

or an enantiomer, diastereomer, tautomer, or pharmaceutically acceptable salt or solvate thereof, wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl;

$R_6$ is hydrogen, halogen, cyano, nitro, $CF_3$, $OCF_3$, alkyl or substituted alkyl, heterocycle or substituted heterocycle, aryl or substituted aryl, or $OR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, $R_1$ is hydrogen. In certain other embodiments, $R_3$ is hydrogen. In yet other embodiments, $R_1$ and $R_3$ are each independently hydrogen. In yet other embodiments, $R_6$ is hydrogen or $C_{1-4}$ alkyl or substituted $C_{1-4}$ alkyl. In yet other embodiments, $R_6$ is hydrogen. In yet other embodiments, $R_1$, $R_3$ and $R_6$ are each independently hydrogen. In yet other embodiments, $R_4$, $R_7$ and $R_8$ are each independently hydrogen. In yet other embodiments, $R_1$, $R_3$, $R_4$, $R_6$, $R_7$ and $R_8$ are each independently hydrogen.

In certain embodiments, $R_5$ is alkylaryl or alkylheteroaryl, in which said alkyl, aryl or heteroaryl may be optionally substituted. In certain other embodiments, $R_5$ is aryl or substituted aryl. In yet other embodiments, $R_5$ is phenyl or substituted phenyl. In yet other embodiments, $R_5$ is heterocycle or substituted heterocycle. In yet other embodiments, $R_5$ is heteroaryl or substituted heteroaryl. In yet other embodiments, $R_5$ is pyridine or substituted pyridine.

In certain embodiments, $R_2$ is aryl or substituted aryl. In certain other embodiments, $R_2$ is heteroaryl or substituted heteroaryl. In yet other embodiments, $R_2$ is a 5- or 6-membered aromatic ring containing at least one heteroatom selected from N, O and S.

In one aspect, the present invention provides a compound of formula II,

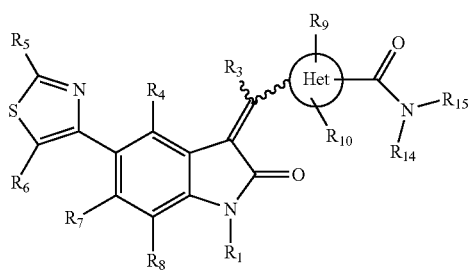

or an enantiomer, diastereomer, tautomer, or pharmaceutically acceptable salt or solvate thereof, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle;

n is an integer selected from 2, 3, 4, 5 and 6;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, $R_1$ is hydrogen. In certain other embodiments, $R_3$ is hydrogen. In yet other embodiments, $R_1$ and $R_3$ are each independently hydrogen. In yet other embodiments, $R_e$ is hydrogen or $C_{1-4}$ alkyl or substituted $C_{1-4}$ alkyl. In yet other embodiments, $R_6$ is hydrogen. In yet other embodiments, $R_1$, $R_3$ and $R_6$ are each independently hydrogen. In yet other embodiments, $R_4$, $R_7$ and $R_8$ are each independently hydrogen. In yet other embodiments, $R_1$, $R_3$, $R_4$, $R_6$, $R_7$ and $R_8$ are each independently hydrogen.

In certain embodiments, $R_5$ is alkylaryl or alkylheteroaryl, in which said alkyl, aryl or heteroaryl may be optionally substituted. In certain other embodiments, $R_5$ is aryl or substituted aryl. In yet other embodiments, $R_5$ is phenyl or substituted phenyl. In yet other embodiments, $R_5$ is heterocycle or substituted heterocycle. In yet other embodiments, $R_5$ is heteroaryl or substituted heteroaryl. In yet other embodiments, $R_5$ is pyridine or substituted pyridine.

In certain embodiments, $R_9$ and $R_{10}$ are each independently hydrogen or $C_{1-4}$ alkyl or substituted $C_{1-4}$ alkyl. In certain other embodiments, $R_9$ and $R_{10}$ are each independently methyl.

In certain embodiments, $R_{14}$ and $R_{15}$ are independently hydrogen, alkyl or substituted alkyl, or said $R_{14}$ and $R_{15}$ together with the N to which they are bonded optionally form a 3-membered, 4-membered, 5-membered, 6-membered, or 7-membered saturated substituted or unsubstituted heterocycle. In certain other embodiments, $R_{14}$ and $R_{15}$ are independently hydrogen, $C_{1-4}$ alkyl or substituted $C_{1-4}$ alkyl, or said $R_{14}$ and $R_{15}$ together with the N to which they are bonded form a substituted or unsubstituted

wherein m is an integer selected from the group consisting of 1, 2, 3, 4 and 5. In yet other embodiments, $R_{14}$ and $R_{15}$ together with the N to which they are bonded form a 6-membered or 7-membered saturated substituted or unsubstituted heterocycle, optionally containing an additional heteroatom selected from N, O and S. In yet other embodiments, $R_{14}$ and $R_{15}$ together with the N to which they are bonded form a 6-membered saturated substituted or unsubstituted heterocycle, optionally containing an additional heteroatom selected from N.

In yet another aspect, the invention provides a compound of formula III,

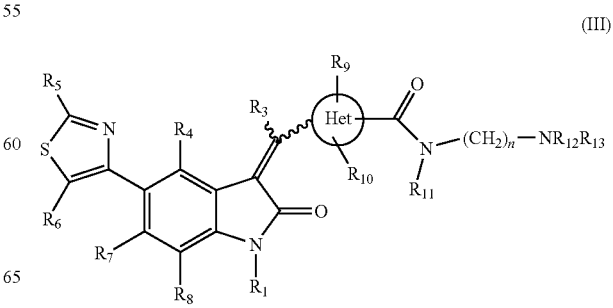

or an enantiomer, diastereomer, tautomer, or pharmaceutically acceptable salt or solvate thereof, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_e$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{11}$ is hydrogen or $C_{1-4}$ alkyl;

$R_{12}$ and $R_{13}$ are independently hydrogen, alkyl or substituted alkyl, cycloalkyl or substituted cycloalkyl, heterocycle or substituted heterocycle, or aryl or substituted aryl, or said $R_{12}$ and $R_{13}$ together with the N to which they are bonded optionally form a heterocycle or substituted heterocycle;

n is an integer selected from 2, 3, 4, 5 and 6;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, $R_1$ is hydrogen. In certain other embodiments, $R_3$ is hydrogen. In yet other embodiments, $R_1$ and $R_3$ are each independently hydrogen. In yet other embodiments, $R_6$ is hydrogen or $C_{1-4}$ alkyl or substituted $C_{1-4}$ alkyl. In yet other embodiments, $R_6$ is hydrogen. In yet other embodiments, $R_1$, $R_3$ and $R_6$ are each independently hydrogen. In yet other embodiments, $R_4$, $R_7$ and $R_8$ are each independently hydrogen. In yet other embodiments, $R_1$, $R_3$, $R_4$, $R_6$, $R_7$ and $R_8$ are each independently hydrogen.

In certain embodiments, $R_5$ is alkylaryl or alkylheteroaryl, in which said alkyl, aryl or heteroaryl may be optionally substituted. In certain other embodiments, $R_5$ is aryl or substituted aryl. In yet other embodiments, $R_5$ is phenyl or substituted phenyl. In yet other embodiments, $R_5$ is heterocycle or substituted heterocycle. In yet other embodiments, $R_5$ is heteroaryl or substituted heteroaryl. In yet other embodiments, $R_5$ is pyridine or substituted pyridine.

In certain embodiments, $R_9$ and $R_{10}$ are each independently hydrogen or $C_{1-4}$ alkyl or substituted $C_{1-4}$ alkyl. In certain other embodiments, $R_9$ and $R_{10}$ are each independently methyl.

In certain embodiments, $R_{11}$ is hydrogen. In certain other embodiments, n is 2 or 3.

In certain embodiments, $R_{12}$ and $R_{13}$ are independently hydrogen, alkyl or substituted alkyl, or said $R_{12}$ and $R_{13}$ together with the N to which they are bonded optionally form a 3-membered, 4-membered, 5-membered, 6-membered, or 7-membered saturated substituted or unsubstituted heterocycle. In certain other embodiments, $R_{12}$ and $R_{13}$ are independently hydrogen, $C_{1-4}$ alkyl or substituted $C_{1-4}$ alkyl, or said $R_{12}$ and $R_{13}$ together with the N to which they are bonded form a substituted or unsubstituted

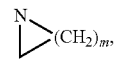

wherein m is an integer selected from the group consisting of 1, 2, 3, 4 and 5.

In yet other embodiments, $R_{12}$ and $R_{13}$ are each independently ethyl. In yet other embodiments, $R_{12}$ and $R_{13}$ together with the N to which they are bonded form a 6-membered or 7-membered saturated substituted or unsubstituted heterocycle, optionally containing an additional heteroatom selected from N, O and S. In yet other embodiments, $R_{12}$ and $R_{13}$ together with the N to which they are bonded form a 6-membered saturated substituted or unsubstituted heterocycle, optionally containing an additional heteroatom selected from N.

In yet another aspect, the invention provides a compound of formula IV,

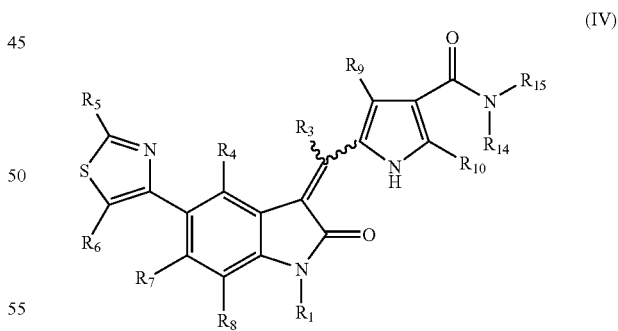

(IV)

or an enantiomer, diastereomer, tautomer, or pharmaceutically acceptable salt or solvate thereof, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(\!=\!O)_2R_e$, $S(\!=\!O)_2OR_e$, $C(\!=\!O)OR_d$, $C(\!=\!O)R_a$, or $C(\!=\!O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(\!=\!O)R_e$, $S(\!=\!O)_2R_e$, $P(\!=\!O)_2R_e$, $S(\!=\!O)_2OR_e$, $P(\!=\!O)_2OR_e$, $NR_bR_c$, $NR_bS(\!=\!O)_2R_e$, $NR_bP(\!=\!O)_2R_e$, $S(\!=\!O)_2NR_bR_c$, $P(\!=\!O)_2NR_bR_c$, $C(\!=\!O)OR_e$, $C(\!=\!O)R_a$, $C(\!=\!O)NR_bR_c$, $OC(\!=\!O)R_a$, $OC(\!=\!O)NR_bR_c$, $NR_bC(\!=\!O)OR_e$, $NR_dC(\!=\!O)NR_bR_c$, $NR_dS(\!=\!O)_2NR_bR_c$, $NR_dP(\!=\!O)_2NR_bR_c$, $NR_bC(\!=\!O)R_a$, or $NR_bP(\!=\!O)_2R_e$;

$R_5$ is alkyl or substituted alkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$, and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, $R_1$ is hydrogen. In certain other embodiments, $R_3$ is hydrogen. In yet other embodiments, $R_1$ and $R_3$ are each independently hydrogen. In yet other embodiments, $R_6$ is hydrogen or $C_{1-4}$ alkyl or substituted $C_{1-4}$ alkyl. In yet other embodiments, $R_6$ is hydrogen. In yet other embodiments, $R_1$, $R_3$ and $R_6$ are each independently hydrogen. In yet other embodiments, $R_4$, $R_7$ and $R_8$ are each independently hydrogen. In yet other embodiments, $R_1$, $R_3$, $R_4$, $R_6$, $R_7$ and $R_8$ are each independently hydrogen.

In certain embodiments, $R_5$ is alkylaryl or alkylheteroaryl, in which said alkyl, aryl or heteroaryl may be optionally substituted. In certain other embodiments, $R_5$ is aryl or substituted aryl. In yet other embodiments, $R_5$ is phenyl or substituted phenyl. In yet other embodiments, $R_5$ is heterocycle or substituted heterocycle. In yet other embodiments, $R_5$ is heteroaryl or substituted heteroaryl. In yet other embodiments, $R_5$ is pyridine or substituted pyridine.

In certain embodiments, $R_9$ and $R_{10}$ are each independently hydrogen or $C_{1-4}$ alkyl or substituted $C_{1-4}$ alkyl. In certain other embodiments, $R_9$ and $R_{10}$ are each independently methyl.

In certain embodiments, $R_{14}$ and $R_{15}$ are independently hydrogen, alkyl or substituted alkyl, or said $R_{14}$ and $R_{15}$ together with the N to which they are bonded optionally form a 3-membered, 4-membered, 5-membered, 6-membered, or 7-membered saturated substituted or unsubstituted heterocycle. In certain other embodiments, $R_{14}$ and $R_{15}$ are independently hydrogen, $C_{1-4}$ alkyl or substituted $C_{1-4}$ alkyl, or said $R_{14}$ and $R_{15}$ together with the N to which they are bonded form a substituted or unsubstituted

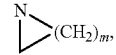

wherein m is an integer selected from the group consisting of 1, 2, 3, 4 and 5. In yet other embodiments, $R_{14}$ and $R_{15}$ together with the N to which they are bonded form a 6-membered or 7-membered saturated substituted or unsubstituted heterocycle, optionally containing an additional heteroatom selected from N, O and S. In yet other embodiments, $R_{14}$ and $R_{15}$ together with the N to which they are bonded form a 6-membered saturated substituted or unsubstituted heterocycle, optionally containing an additional heteroatom selected from N.

In yet another aspect, the invention provides a compound of formula V,

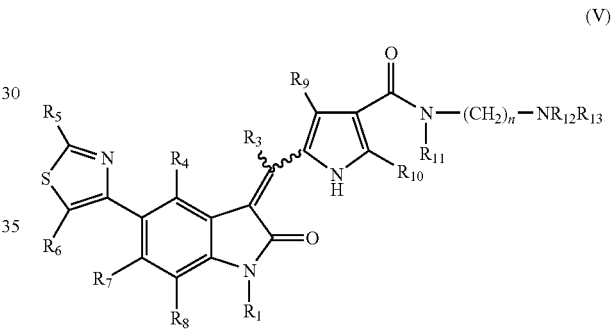

(V)

or an enantiomer, diastereomer, tautomer, or pharmaceutically acceptable salt or solvate thereof, wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(\!=\!O)_2R_e$, $S(\!=\!O)_2OR_e$, $C(\!=\!O)OR_d$, $C(\!=\!O)R_a$, or $C(\!=\!O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(\!=\!O)R_e$, $S(\!=\!O)_2R_e$, $P(\!=\!O)_2R_e$, $S(\!=\!O)_2OR_e$, $P(\!=\!O)_2OR_e$, $NR_bR_c$, $NR_bS(\!=\!O)_2R_e$, $NR_bP(\!=\!O)_2R_e$, $S(\!=\!O)_2NR_bR_c$, $P(\!=\!O)_2NR_bR_c$, $C(\!=\!O)OR_e$, $C(\!=\!O)R_a$, $C(\!=\!O)NR_bR_c$, $OC(\!=\!O)R_a$, $OC(\!=\!O)NR_bR_c$, $NR_bC(\!=\!O)OR_e$, $NR_dC(\!=\!O)NR_bR_c$, $NR_dS(\!=\!O)_2NR_bR_c$, $NR_dP(\!=\!O)_2NR_bR_c$, $NR_bC(\!=\!O)R_a$, or $NR_bP(\!=\!O)_2R_e$;

$R_5$ is substituted alkyl, heterocycle or substituted heterocycle, aryl or substituted aryl;

R$_6$ and R$_9$ are each independently hydrogen, halogen, cyano, nitro, CF$_3$, OCF$_3$, alkyl or substituted alkyl, heterocycle or substituted heterocycle, aryl or substituted aryl, or OR$_a$;

R$_{11}$ is hydrogen or C$_{1-4}$ alkyl;

R$_{12}$ and R$_{13}$ are independently hydrogen, alkyl or substituted alkyl, cycloalkyl or substituted cycloalkyl, heterocycle or substituted heterocycle, or aryl or substituted aryl, or said R$_{12}$ and R$_{13}$ together with the N to which they are bonded optionally form a heterocycle or substituted heterocycle;

n is an integer selected from 2, 3, 4, 5 and 6;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In certain embodiments, R$_1$ is hydrogen. In certain other embodiments, R$_3$ is hydrogen. In yet other embodiments, R$_1$ and R$_3$ are each independently hydrogen. In yet other embodiments, R$_6$ is hydrogen or C$_{1-4}$ alkyl or substituted C$_{1-4}$ alkyl. In yet other embodiments, R$_6$ is hydrogen. In yet other embodiments, R$_1$, R$_3$ and R$_6$ are each independently hydrogen. In yet other embodiments, R$_4$, R$_7$ and R$_8$ are each independently hydrogen. In yet other embodiments, R$_1$, R$_3$, R$_4$, R$_6$, R$_7$ and R$_8$ are each independently hydrogen.

In certain embodiments, R$_5$ is alkylaryl or alkylheteroaryl, in which said alkyl, aryl or heteroaryl may be optionally substituted. In certain other embodiments, R$_5$ is aryl or substituted aryl. In yet other embodiments, R$_5$ is phenyl or substituted phenyl. In yet other embodiments, R$_5$ is heterocycle or substituted heterocycle. In yet other embodiments, R$_5$ is heteroaryl or substituted heteroaryl. In yet other embodiments, R$_5$ is pyridine or substituted pyridine.

In certain embodiments, R$_9$ and R$_{10}$ are each independently hydrogen or C$_{1-4}$ alkyl or substituted C$_{1-4}$ alkyl. In certain other embodiments, R$_9$ and R$_{10}$ are each independently methyl.

In certain embodiments, R$_{11}$ is hydrogen. In certain other embodiments, n is 2 or 3.

In certain embodiments, R$_{12}$ and R$_{13}$ are independently hydrogen, alkyl or substituted alkyl, or said R$_{12}$ and R$_{13}$ together with the N to which they are bonded optionally form a 3-membered, 4-membered, 5-membered, 6-membered, or 7-membered saturated substituted or unsubstituted heterocycle. In certain other embodiments, R$_{12}$ and R$_{13}$ are independently hydrogen, C$_{1-4}$ alkyl or substituted C$_{1-4}$ alkyl, or said R$_{12}$ and R$_{13}$ together with the N to which they are bonded form a substituted or unsubstituted $$\underset{\diagup}{N}(CH_2)_m,$$

wherein m is an integer selected from the group consisting of 1, 2, 3, 4 and 5.

In yet other embodiments, R$_{12}$ and R$_{13}$ are each independently ethyl. In yet other embodiments, R$_{12}$ and R$_{13}$ together with the N to which they are bonded form a 6-membered or 7-membered saturated substituted or unsubstituted heterocycle, optionally containing an additional heteroatom selected from N, O and S. In yet other embodiments, R$_{12}$ and R$_{13}$ together with the N to which they are bonded form a 6-membered saturated substituted or unsubstituted heterocycle, optionally containing an additional heteroatom selected from N.

In yet another aspect, the invention provides a compound selected from the group consisting of:

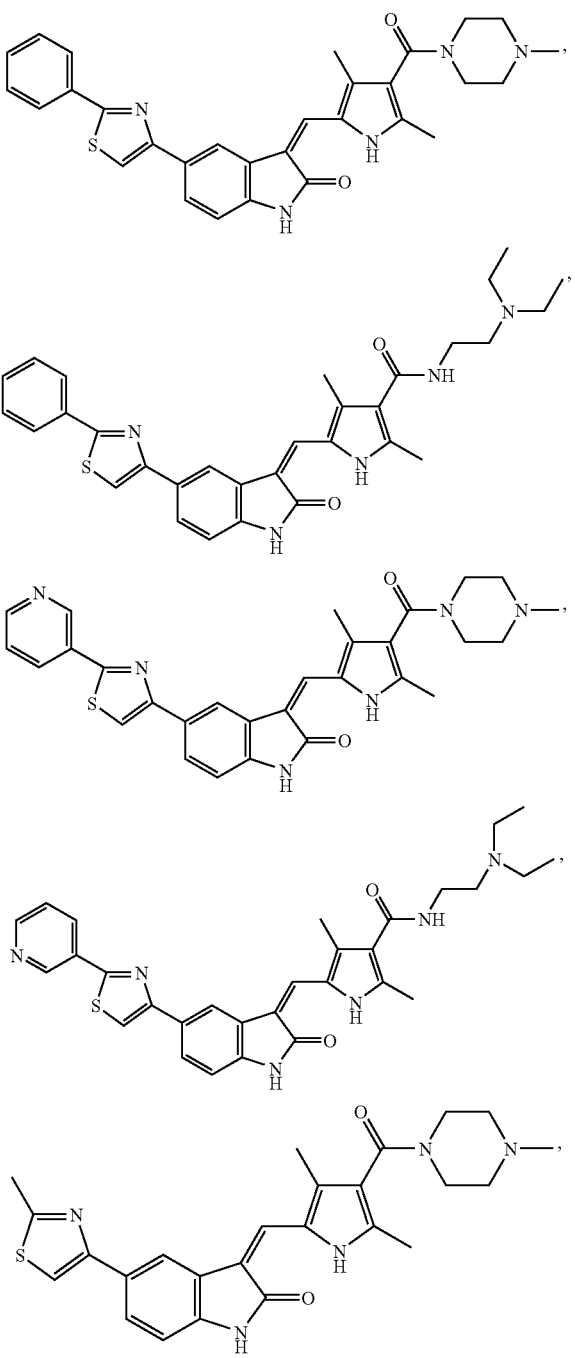

-continued

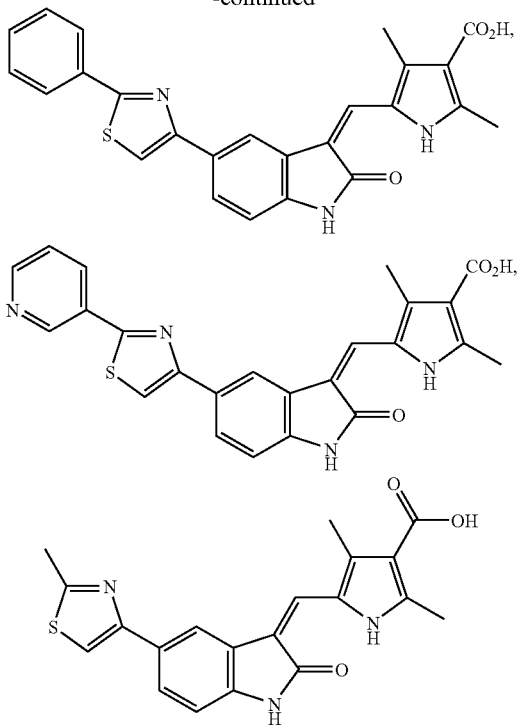

and an enantiomer, diastereomer, tautomer, or pharmaceutically acceptable salt or solvate thereof.

C. Uses, Formulation and Administration

The present invention also provides, in part, a method of treating, preventing or ameliorating a protein kinase related disorder in a mammal, comprising administering to the mammal in need thereof a therapeutically effective amount of a pharmaceutical composition comprising a compound of the present invention as described hereinabove. The mammal may be in need of the treatment or the treatment may be administered prophylacticly for prevention or for amelioration of the protein kinase related disorder.

A "protein kinase related disorder" is any disease or deleterious condition in which a protein kinase plays a role. Examples include a serine-threonine kinase related disorder, a receptor tyrosine kinase related disorder, a non-receptor tyrosine kinase related disorder, an EGFR related disorder, an IGFR related disorder, a PDGFR related disorder and a flk related disorder. The compounds of the present invention may be used for any of these protein kinase related disorders.

In certain embodiments, the protein kinase related disorder is a cancer such as lung cancer, bladder cancer, head and neck cancer, melanoma, ovarian cancer, prostate cancer, breast cancer, small-cell lung cancer, glioma, colorectal cancer, non-small cell lung cancer, genitourinary cancer, pancreatic cancer, thyroid cancer, Hodgkin's lymphoma, non-Hodgkin's lymphoma, gastrointestinal cancer, gastric cancer, hepatoma, gastrointestinal stromal tumor, squamous cell carcinoma, renal cell carcinoma, astrocytoma, Kaposi's sarcoma, chronic myelogenous leukemia, acute myelogenous leukemia, myeloproliferative disorders, and glioblastoma.

According to one or more embodiments of the present invention, "cancer stem cell" ("CSC") or "cancer stem cells" ("CSCs") refer to a minute population of cancer cells that have self-renewal capability and are tumorigenic. They are also called "Cancer Initiating Cells", "Tumor Initiating Cells", "Cancer Stem-Like Cells", "Stem-Like Cancer Cells", "aggressive cancer cells", and "super malignant cancer cells", etc. The methods of isolating these cells include but not limited to enrichment by their ability of efflux Hoechst 33342, enrichment of surface markers such as CD133, CD44, and others, and enrichment by their tumorigenic property.

The term "CSCPK" or "CSCPKs" refer to protein kinase(s) that are essential for cancer stem cell survival or self-renewal.

In certain embodiments, the protein kinase is CSCPK. The compounds of the present invention are particularly useful for the treatment, prevention or amelioration of cancer, such as lung cancer, bladder cancer, head and neck cancer, melanoma, ovarian cancer, prostate cancer, breast cancer, small-cell lung cancer, glioma, colorectal cancer, non-small-cell lung cancer, genitourinary cancer, pancreatic cancer, thyroid cancer, Hodgkin's lymphoma, non-Hodgkin's lymphoma, gastrointestinal cancer, gastric cancer, hepatoma, gastrointestinal stromal tumor, squamous cell carcinoma, renal cell carcinoma, astrocytoma, Kaposi's sarcoma, chronic myelogenous leukemia, acute myelogenous leukemia, myeloproliferative disorders, and glioblastoma, by inhibiting CSCPKs.

In yet other embodiments, the protein kinase includes serine-threonine kinases, receptor tyrosine kinases and non-receptor tyrosine kinases.

In yet other embodiments, the protein kinase related disorder includes diabetes, an autoimmune disorder, a hyperproliferation disorder, angiogenesis, an inflammatory disorder, an immunological disorder, a cardiovascular disorder, restenosis, fibrosis, psoriasis, von Heppel-Lindau disease, osteoarthritis, neurodegeneration, infection, and rheumatoid arthritis.

The present invention provides, in part, a method of inhibiting/reducing/diminishing cancer stem cell survival and/or proliferation, self-renewal in a mammal by inhibiting or decreasing unwanted activity of CSCPKs.

The present invention also provides, in part, a method of inhibiting cancer stem cell niche, or stromal cell signaling by targeting CSCPKs.

The present invention further provides, in part, a method of treating cancer, inhibiting/reducing/diminishing cancer stem cell survival and/or proliferation.

The present invention also provides, in part, a method of modulating the catalytic activity of a protein kinase. The method comprises contacting said protein kinase with a compound of the present invention, or a pharmaceutically-acceptable salt thereof. In certain embodiments, the protein kinase includes a serine-threonine kinase, a receptor tyrosine kinase and a non-receptor tyrosine kinase.

The present invention also provides, in part, a pharmaceutical composition comprising a compound of the present invention as described hereinabove, or an enantiomer, diastereomer, tautomer, or pharmaceutically acceptable salt or solvate thereof, and a pharmaceutically-acceptable excipient, carrier, or diluent.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the mammal being treated and the particular mode of administration. The amount of active ingredient, which can be combined with a carrier material to produce a single dosage form will generally be that amount of the compound which produces a therapeutic effect. Generally, out of 100%, this amount will range, for example, from about 0.1% to about 25% of active ingredient.

Therapeutic compositions or formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the alcohol or inhibitor according to the invention is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents. Suspensions, in addition to the alcohols or inhibitors according to the invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more alcohols or inhibitors according to the invention, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention. Formulations of the present invention which are suitable for vaginal administration also include pessaries, tampons, creams, gels, pastes, foams or spray formulations containing such carriers as are known in the art to be appropriate.

Dosage forms for the topical or transdermal administration of an alcohol or other inhibitor according to the invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an alcohol or other inhibitor according to the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more alcohols or inhibitors according to the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of the alcohol or inhibitor according to the invention, it is desirable to slow the absorption of the alcohol or inhibitor from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered composition is accomplished by dissolving or suspending the alcohol or inhibitor in an oil vehicle. One strategy for depot injections includes the use of polyethylene oxide-polypropylene oxide copolymers wherein the vehicle is fluid at room temperature and solidifies at body temperature.

The pharmaceutical compounds of this invention may be administered alone, or simultaneously, subsequently or sequentially with one or more active agents, other pharmaceutical agents, or with other anti-cancer or cytotoxic agent as described hereinabove, as well as in combination with a pharmaceutically-acceptable excipient, carrier, or diluent as described above.

The amount of pharmacological agent in the oral unit dosage form, with as a single or multiple dosage, is an amount that is effective for treating a neurological disorder. As one of skill in the art will recognize, the precise dose to be employed will depend on a variety of factors, examples of which include the condition itself, the seriousness of the condition being treated, the particular composition used, as well as various physical factors related to the individual being treated. In vitro or in vivo assays can optionally be employed to help identify optimal dosage ranges.

The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compounds of the invention or a physiologically acceptable salt thereof calculated as the free base, the compound being administered 1 to 4 times per day. Suitably the compounds will be administered for a period of continuous therapy, for example for a week or more.

D. Chemical Synthesis

The compounds of the present invention can be prepared using the methods described below, together with synthetic methods known one skilled in the art of organic synthesis, or variations thereof. The reactions are performed in solvents appropriate to the reagents and materials employed and are suitable for transformations being effected. The starting materials for the examples contained herein are either commercially available or are readily prepared by standard methods from known materials. For example, the following reactions are illustrations but not limitations of the preparation of some of the starting materials and examples used herein. The various substituents on compounds of formulae as shown in Schemes 1 and 2 are as defined hereinabove.

As shown in Scheme 1, a compound of formula VII can react with a compound of formula VIII to under conditions effective (e.g., heating) to provide a thiazole-substituted compound of formula VI. The compound of formula VI can further react with a compound of formula IX in the presence of a base (e.g., piperidine) to give a compound of formula VI.

Scheme 1

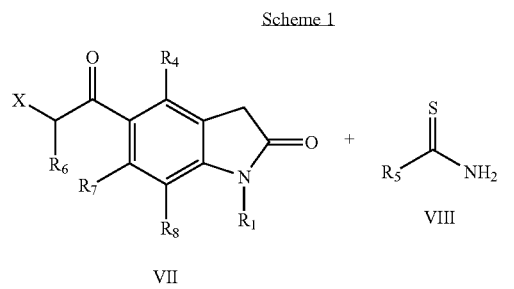

VII

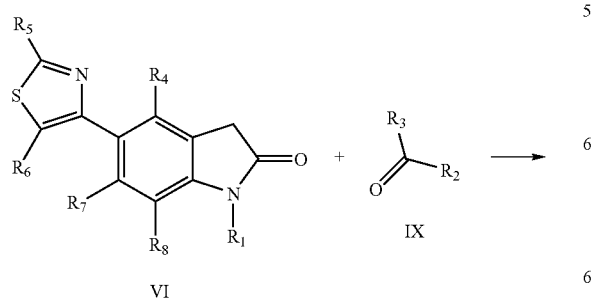

VI

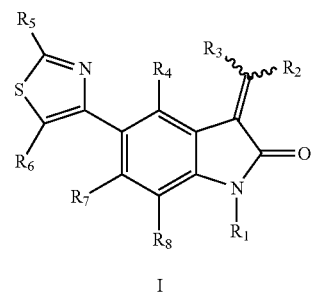

I

A compound of formula II can be prepared in accordance with Scheme 2. The compound of formula VI can react with a compound of formula X in the presence of a base (e.g., piperidine) to give a compound of formula XI. The compound of formula XI can further react with an amine formula of XII, in the presence of a peptide coupling agent and a base, to provide the compound of formula II.

Scheme 2

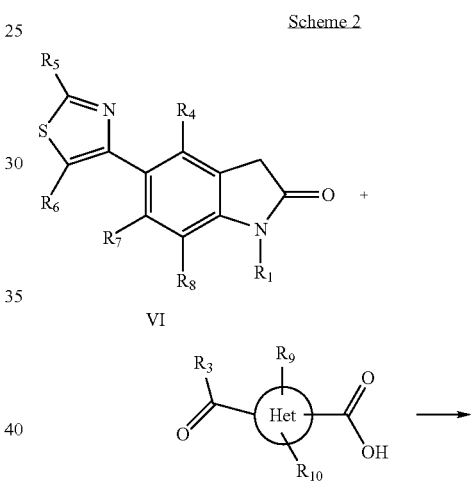

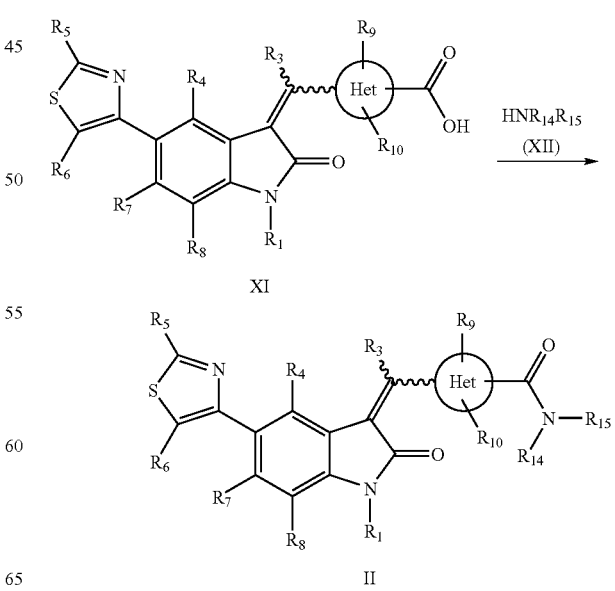

II

The following examples further illustrate, without limitation, the preparation for the compounds of the present invention.

EXAMPLES

Example 1

Preparation of Compound 7-1

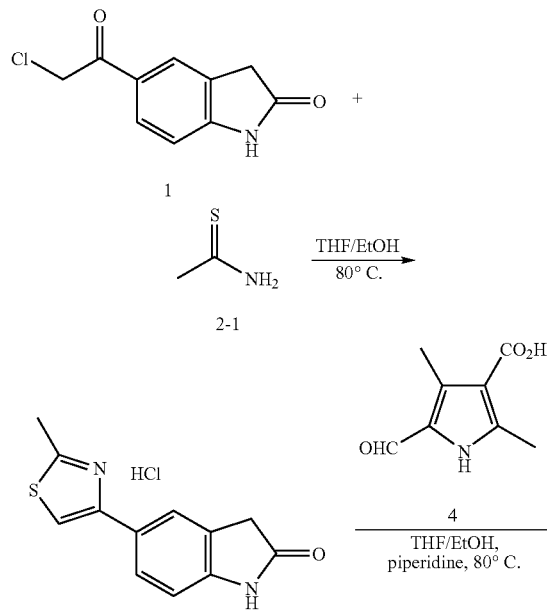

To a suspension of 5-chloroacetyloxindole 1 (42 mg, 0.2 mmol) in EtOH/THF (2 mL/1 mL) was added thioacetamide 2-1 (15 mg, 0.2 mmol). The mixture was heated at 80 C for 16 h before cooled down. The solution was concentrated in vacuo to get an orange solid 3. $^1$H NMR (300 MHz, DMSO-d6) δ 10.50 (br. S, 1H), 7.72-7.80 (m, 2H), 7.33 (s, 1H), 7.16 (s, 1H), 6.86 (d, 1H, J=8.63 Hz), 3.42-4.54 (m, 2H); MS m/z 231.10 (M+H).

To a solution of 3 (53 mg, 0.2 mmol) in EtOH/THF (2 mL/1 mL) (or use the above reaction mixture in EtOH/THF (2 mL/1 mL) solution) was added 5-formyl-2,4-dimethyl-1H-pyrrole-3-carboxylic acid 4 (33.4 mg, 0.2 mmol) and piperidine (21.8 μL). The mixture was heated at 80 C for 2 hours. After cooled down to room temperature, the reaction mixture was filtrated and washed with EtOH (1 mL) to get the reddish solid 5. $^1$H NMR (300 MHz, DMSO-d6) δ 13.80 (s, 1H), 12.10 (br.s, 1H), 11.08 (s, 1H), 8.35 (s, 1H), 7.85 (s, 1H), 7.78-7.81 (m, 2H), 6.94 (d, 1H, J=8.11 Hz), 2.74 (s, 3H), 2.56 (s, 3H), 2.52 (s, 3H); MS m/z 380.21 (M+H).

To a solution of 5 (20 mg, 0.052 mmol) in DMF (1.5 mL) was added HATU (24 mg, 0.063 mmol), diisopropylethylamine (30 μL, 0.168 mmol), and 1-methylpiperazine 6-1 (10 μL, 0.090 mmol). The mixture was stirred at room temperature for 16 hours then concentrated in vacuo. The residue was added CH$_2$Cl$_2$ (2 mL) and extracted with H$_2$O (3×1.5 mL). The organic layer was dried over Na$_2$SO$_4$ and concentrated in vacuo. The residue was purified by column chromatography (CH$_2$Cl$_2$/MeOH/Et$_3$N) to get a yellow solid 7-1. $^1$H NMR (300 MHz, DMSO-d6) δ 11.00 (s, 1H), 8.30 (s, 1H), 7.83 (s, 1H), 7.65-7.78 (m, 2H), 6.94 (d, 1H, J=8.18 Hz), 3.02-3.20 (m, 4H), 2.74 (s, 3H), 2.5-2.58 (m, 4H), 2.5 (s, 6H), 2.3 (s, 3H); MS m/z 462.20 (M+H).

Example 2

Preparation of Compound 10-1

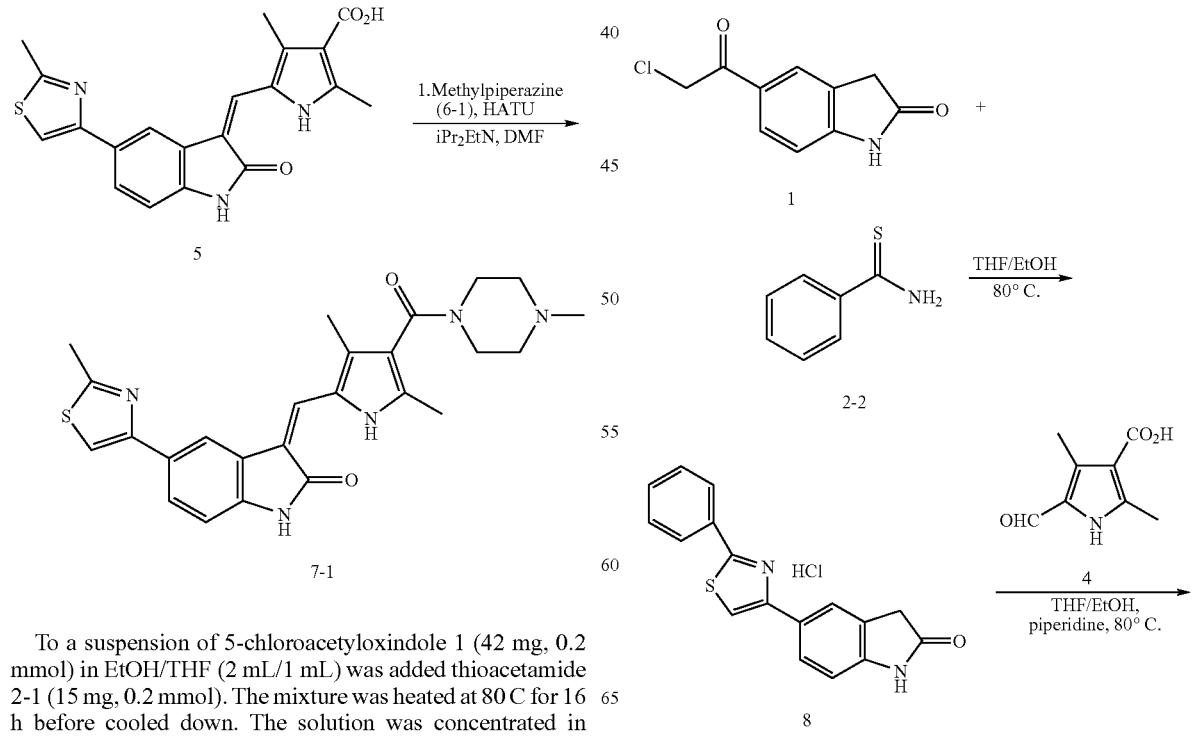

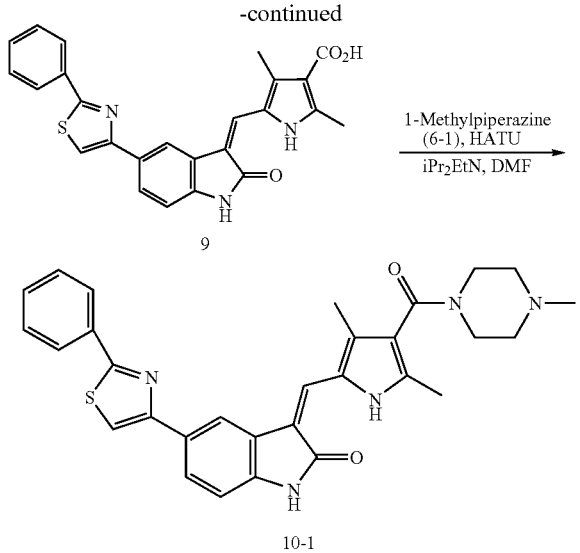

To a suspension of 5-chloroacetyloxindole 1 (820 mg, 4 mmol) in EtOH/THF (20 mL/20 mL) was added thiobenzamide 2-2 (550 mg, 4 mmol). The mixture was heated at 80 C for 16 h before cooled down. The solution was concentrated in vacuo to get an orange solid 8. MS m/z 293.20 (M+H).

To this solid 8 was added EtOH/THF (20 mL/20 mL) (or use the above reaction mixture), 5-formyl-2,4-dimethyl-1H-pyrrole-3-carboxylic acid 4 (668 mg, 4 mmol) and piperidine (400 μL). The mixture was heated at 80 C for 5 hours. After cooled down to room temperature, the reaction mixture was filtrated and washed with EtOH (1 mL) to get the orange solid 9. $^1$H NMR (300 MHz, DMSO-d6) δ 13.80 (s, 1H), 12.40 (s, 1H), 11.10 (s, 1H), 8.47 (s, 1H), 8.07-8.12 (m, 3H), 7.94 (d, 1H, J=8.00 Hz), 7.86 (s, 1H), 7.55-7.6 (m, 3H), 7.01 (d, 1H, J=8.10 Hz), 2.59 (s, 3H), 2.57 (s, 3H); MS m/z 442.20 (M+H).

To a solution of 9 (34 mg, 0.077 mmol) in DMF (1.5 mL) was added HATU (35 mg, 0.092 mmol), diisopropylethylamine (30 μL, 0.168 mmol), and 1-methylpiperazine 6-1 (15 μL, 0.13 mmol). The mixture was stirred at room temperature for 16 hours then concentrated in vacuo. The residue was added $CH_2Cl_2$ (2 mL) and extracted with $H_2O$ (3×1.5 mL). The organic layer was dried over $Na_2SO_4$ and concentrated in vacuo. The residue was purified by column chromatography ($CH_2Cl_2$/MeOH/$Et_3N$) to get a yellow solid 10-1. $^1$H NMR (300 MHz, DMSO-d6) δ 13.68 (s, 1H), 11.10 (s, 1H), 8.44 (s, 1H), 8.07-8.10 (m, 3H), 7.91 (d, 1H, J=8.00 Hz), 7.80 (s, 1H), 7.68-7.76 (m, 2H), 7.52-7.58 (m, 1H), 7.01 (d, 1H, J=8.10 Hz), 3.02-3.15 (m, 4H), 2.52-2.58 (m, 4H), 2.5 (s, 3H), 2.35 (s, 3H), 2.33 (s, 3H); MS m/z 524.20 (M+H).

Example 3

Preparation of Compound 10-2

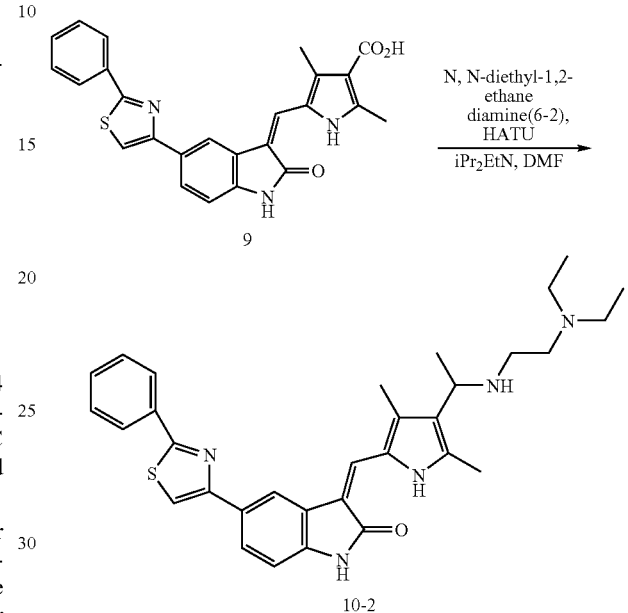

To a solution of 9 (1.55 g, 3.5 mmol) in DMF (130 mL) was added HATU (1.6 g, 4.2 mmol), diisopropylethylamine (1.6 mL, 9.2 mmol), and N,N-diethyl-1,2-ethanediamine 6-2 (0.6 mL, 4.2 mmol). The mixture was stirred at room temperature for 16 hours then concentrated in vacuo. The residue was added $CH_2Cl_2$ (800 mL) and extracted with $H_2O$ (200 mL), saturated $NaHCO_3$ (200 mL), $H_2O$ (2×200 mL), and brine (200 mL). The organic layer was dried over $Na_2SO_4$ and concentrated in vacuo. The residue was added small amount of MeOH and filtration to get a yellow solid 10-2. $^1$H NMR (300 MHz, DMSO-d6) δ 13.70 (s, 1H), 11.10 (s, 1H), 8.44 (s, 1H), 8.07-8.10 (m, 3H), 7.92 (d, 1H, J=8.10 Hz), 7.81 (s, 1H), 7.3-7.6 (m, 3H), 7.00 (d, 1H, J=8.10 Hz), 3.2-3.3 (m, 2H), 2.5-2.6 (m, 6H), 2.51 (s, 3H), 2.48 (s, 3H), 1.00 (t, 6H, J=6.90 Hz); MS m/z 540.20 (M+H).

Example 4

Preparation of Compound 13-1

Scheme D

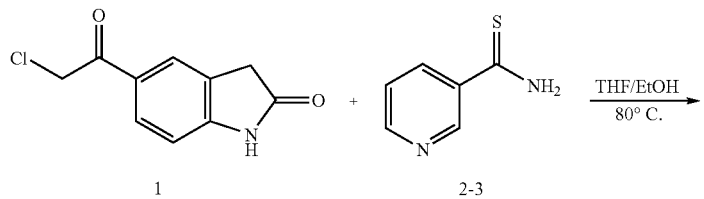

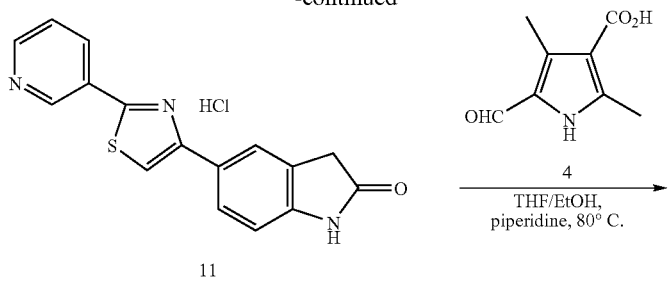

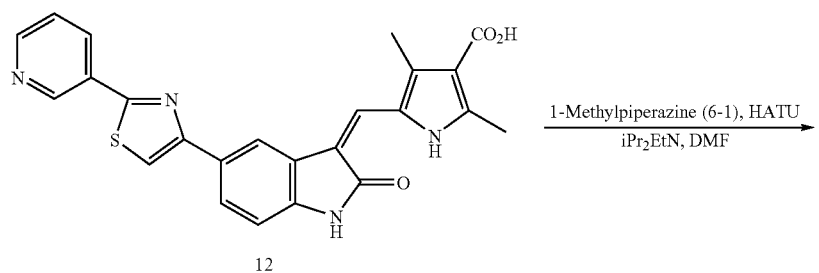

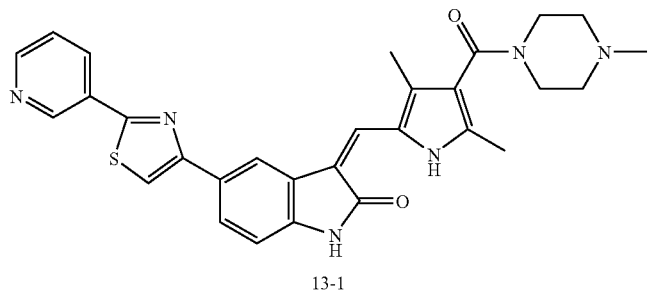

To a suspension of 5-chloroacetyloxindole 1 (42 mg, 0.2 mmol) in EtOH/THF (1 mL/1 mL) was added thionicotinamide 2-3 (27.8 mg, 0.2 mmol). The mixture was heated at 80 C for 16 h before cooled down. The solution was concentrated in vacuo to get an orange solid 11. MS m/z 294.20 (M+H).

To this solid 11 was added EtOH/THF (1 mL/1 mL), 5-formyl-2,4-dimethyl-1H-pyrrole-3-carboxylic acid (33.4 mg, 0.2 mmol) and piperidine (21.8 μL). The mixture was heated at 80 C for 2 hours. After cooled down to room temperature, the reaction mixture was concentrated and filtrated to get the orange solid 12. MS m/z 443.20 (M+H).

To a solution of the solid 12 (44 mg, 0.10 mmol) in DMF (1.5 mL) was added HATU (35 mg, 0.12 mmol), diisopropylethylamine (50 μL, 0.33 mmol), and 1-methylpiperazine 6-1 (30 μL, 0.26 mmol). The mixture was stirred at room temperature for 16 hours then concentrated in vacuo. The residue was added $CH_2Cl_2$ (2 mL) and extracted with $H_2O$ (1.5 mL). The organic layer was dried over $Na_2SO_4$ and concentrated in vacuo. The residue was purified by column chromatography ($CH_2Cl_2$/MeOH/$Et_3$N) to get a yellow solid 13-1. $^1$H NMR (400 MHz, DMSO-d6) δ 13.55 (s, 1H), 11.00 (s, 1H), 9.20 (d, 1H, J=1.60 Hz), 8.64 (dd, 1H, J=4.70, 1.60 Hz), 8.35-8.37 (m, 2H), 8.10 (s, 1H), 7.84 (dd, 1H, J=8.00, 1.60 Hz), 7.71 (s, 1H), 7.52 (ddd, J=8.00, 4.70, 0.70 Hz, 1H), 6.92 (d, 1H, J=8.00 Hz), 3.07-3.2 (m, 4H), 2.26 (s, 3H), 2.24 (s, 3H), 2.24-2.3 (m, 4H), 2.13 (s, 3H); MS m/z 525.20 (M+H).

Example 5

Preparation of Compound 13-2

Scheme E

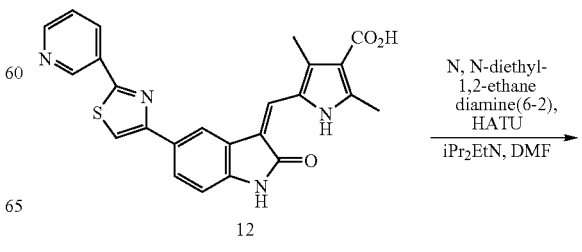

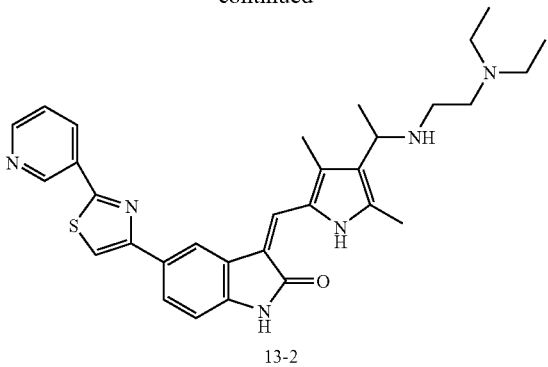

13-2

To a solution of the solid 12 (44 mg, 0.10 mmol) in DMF (1.5 mL) was added HATU (35 mg, 0.12 mmol), diisopropylethylamine (50 μL, 0.33 mmol), and N,N-diethyl-1,2-ethanediamine 6-2 (23 μL, 0.2 mmol). The mixture was stirred at room temperature for 16 hours then concentrated in vacuo. The residue was added $CH_2Cl_2$ (2 mL) and extracted with $H_2O$ (1.5 mL). The organic layer was dried over $Na_2SO_4$ and concentrated in vacuo. The residue was purified by column chromatography ($CH_2Cl_2$/MeOH/$Et_3N$) to get a yellow solid 13-2. $^1$H NMR (400 MHz, DMSO-d6) δ 13.60 (s, 1H), 11.00 (s, 1H), 9.18 (d, 1H, J=1.60 Hz), 8.64 (dd, 1H, J=4.80, 1.60 Hz), 8.33-8.37 (m, 2H), 8.09 (s, 1H), 7.83 (dd, 1H, J=8.00, 1.60 Hz), 7.71 (s, 1H), 7.50 (dd, J=8.00, 4.80 Hz, 1H), 7.36-7.39 (m, 1H), 6.91 (d, 1H, J=8.00 Hz), 3.20 (q, J=7.10 Hz, 4H), 2.4-2.6 (m, 4H), 0.90 (t, J=7.10 Hz, 6H); MS m/z 525.20 (M+H). MS m/z 541.20 (M+H).

Compound 13-2 can be prepared from compound 12 and N,N-diethyl-1,2-ethanediamine 6-2 using a method analogous to that used for the preparation of compound 13-1.

Example 6

Formulation of the Compounds in this Invention

The compounds in this invention can be formulated in the acceptable oral vehicles as solution mixture or as suspension mixture. For example, the 10 mg/ml solution formulation was prepared as followed. 100 mg of Compound 10-2 [as shown in Example 3] was dissolved in 1.25 ml of DMA (dimethylacetamide) by vigorously shaking and sonication. To the resulting solution, were then added 8.75 ml of the mixture solvent consisting of PEG400 and 20% aqueous vitamin E TPGS (60:40) and 75 μl of 2.4 N HCl. The resulting mixture was heated and sonicated in 45° C. water bath until the solution became clear. The 10 mg/ml suspension formulation was prepared as followed. 100 mg of compound 10-2 was suspended in 10 ml of 0.7% citric acid, and became uniform suspension by vigorously shaking and sonication Example 7

Biological Assays

Compounds of the present invention can be tested according to the protocol described.

Cell Culture: HeLa, Dld1, SW480, MDA-MB-231, A549, HT29, A431, PC3, FaDu, HepG2, and H1299 cells (ATCC, Manassas, Va.) were maintained in Dulbecco's Modified Eagle Medium (DMEM) (Invitrogen, Carlsbad, Calif.) supplemented with 10% fetal bovine serum (FBS) (Gemini Bio-Products, West Sacramento, Calif.) and 5% penicillin/streptomycin/amphotercin B (Invitrogen).

Cell Viability Determination: For colony formation assay, cells were plated in 6 well plates at 2000 cells per well. Twenty-four hours after plating, cells were treated with compound. Colonies were allowed to develop for 7-10 days, at which they were stained with modified Giemsa stain (Sigma). Stained colonies were then counted to determine $IC_{50}$.

Western Blot Analysis: Cultured cells were harvested and lysed in whole-cell extract buffer (50 mM Tris-HcL pH 7.5, 150 mM NaCl, 1.0% NP-40, 1 mM EDTA, 0.1 mM sodium orthovanadate, 1× protease inhibitor cocktail (Roche)) by incubation for 30 minutes on ice. Soluble proteins were separated by centrifugation at 13,000×g in a microcentrifuge, and supernatants were stored at −70° C. Proteins were separated by sodium dodecyl sulfate-polyacrylamide gel electrophoresis analysis and transferred to a polyvinylidene difluoride membrane (Biorad, Hercules, Calif.) by electroblotting.

Hoechst Side Population: SW480 cells were removed from the culture dish with trypsin and ethylenediaminetetraacetic acid ("EDTA"), pelleted by centrifugation, washed with phosphate-buffered saline (PBS), and resuspended at 37° C. in Dulbecco's modified Eagle's medium (DMEM) containing 2% FBS and 1 mM 4-(2-hydroxyethyl)-1-piperazineethanesulfonic acid (HEPES). The cells were then labeled with Hoechst 33342 (Invitrogen) at a concentration of 5 μg/mL. The labeled cells were incubated for 120 minutes at 37° C., either alone or with 50 μM verapamil (Sigma-Aldrich, St. Louis). After staining, the cells were suspended in Hanks' balanced saline solution (HBSS; Invitrogen) containing 2% FBS and 1 mM HEPES, passed a through 40 μm mesh filter, and maintained at 4° C. until flow cytometry analysis. The Hoechst dye was excited at 350 nm, and its fluorescence was measured at two wavelengths using a 450 DF10 (450/20 nm band-pass filter) and a 675LP (675 nm long-pass edge filter) optical filter. The gating on forward and side scatter was not stringent, and only debris was excluded (Goodell et al., 1996 J Exp Med 183, 1797-806).

CSC isolation with surface markers: Sorting tumor cells based primarily upon the differential expression of the surface marker(s), such as CD44 or CD133, have accounted for the majority of the highly tumorigenic CSCs described to date. $CD44^{high}$ cells were isolated by FACS according to the methods described in Ponti et al, with slight modification [24]. Briefly, after trypsinization and recovery of cells for 30 minutes at 37° C. in growth media, cells were pelleted at 400×g and were resuspended in PBS with 2% FBS and 1 mM EDTA at 1×10$^6$ cells/mL. Cells were then incubated on ice with a 1:100 dilution of CD44-FITC (BD Biosicences, San Diego, Calif.) for 15 minutes. Alternatively, CD24-PE (BD Biosicences, San Diego, Calif.) (1:100) was utilized for negative selection. After washing three times, cells were resuspended at 2×10$^6$/mL and passed through a 40 μM mesh before sorting.

Immunofluorescence: Cells treated with indicated compound for an indicated time were either fixed in 4% formaldehyde or cold methanol for the detection of Annexin V. Coverslips were air dried and rehydrated in PBS at room temperature for 10 min. Samples were then incubated in blocking buffer (PBS, 5% FBS) for about 10 min. at room temperature in a humid chamber. Cells were incubated overnight at 4° C. with primary antibodies. After washing, the cells were incubated for 1 hour at room temperature with a 1:500 dilution of FITC conjugated anti-rabbit antibody. Images were captured with a Nikon TE200 microscope equipped with epifluorescence and a SPOT mosaic CCD camerapolyclonal Annexin-V-FITC was obtained from Roche, Penzberg, Germany.

Sphere assay: A reliable method of measuring the self-renewal capacity of cell population if the ability to be cultured as spheres in the absence of serum or attachment. $CD44^{high}$ FaDu or Hoechst side population cancer stem cells were cultured in ultra low attachment plates in cancer stem cell media (DMEM/F12, B27 Neurobasal supplement, 20 ng/ml EGF, 10 ng/ml FGF, 4 µg/ml insulin, and 0.4% BSA) to allow spheres formation. Typically, sphere formation was evaluated by microscopy after 10-14 days in culture and spheres with >50 cells were scored.

Murine Xenograft Model: Human prostate cancer xenograft PC3 cells were passaged internally and inoculated into male athymic nude mice s.c. at a level of $8.0 \times 10^6$ cells/mouse. At staging, the tumors were approximately 350 mm³. Tumor dimensions were determined using a digital caliper and tumor volumes were calculated as $[length \times (width)^2/2]$. Similarly, human liver cancer xenograft HepG2 cells were inoculated into female nude mice at a level of $8.0 \times 10^6$ cells/mouse and the treatment began when the tumors were about 700 mm³. Human head and neck cancer xenograft FaDu cells were inoculated into female nude mice at a level of $6.0 \times 10^6$ cells/mouse and the treatment began when the tumors were about 150 mm³.

Test Articles: Compound 10-2 [as shown in Example 3] as a hydrochloride salt was formulated to 10 mg/ml in DMA/PEG400/H₂O (10%:50%:40%) for intraperitoneal administration and was formulated to 10 mg/ml in DMA/PEG400/20% Vitamin E (12.5%/52.5%/35%) for per osl administration.

Test Article Administration: Dosing was done as indicated.

TABLE 1

Summary of Study Groups and Treatment Regimens

| | | | Treatment Regimen | | |
|---|---|---|---|---|---|
| Group | Group ID | N | Test Article | Vehicle | Dose (mg/kg) |
| 1 | Vehicle Control | 5-8 | none | DMA/PEG400/H₂O (or Vit. E) | 0 |
| 2 | 10-2 | 5-8 | 10-2 | DMA/PEG400/H₂O (or Vit. E) | As indicated |

In Life Evaluations: Daily examinations into the health status of each animal were also conducted. Body weights were checked every three days. Food and water was supplied daily according to the animal husbandry procedures of the facility. Treatment producing >20% lethality and or >20% net body weight loss were considered toxic. The results are expressed as mean tumor volume $(mm^3) \pm SE$. P Values<0.05 are considered to be statistically relevant.

Animal Husbandry: Male or female athymic nude mice 4-5 weeks (Charles River Laboratories, Wilmington, Mass.), were acclimated to the animal housing facility for at least 1 week before study initiation. All of the experimental procedures utilized were consistent with the guidelines outlined by the American Physiology Society and the Guide for the Care and Use of Laboratory Animals and were also approved by the Institutional Animal Care and Use Committee of Boston Biomedical Inc. The animals were housed in groups of four in wood chip bedded cages in a room having controlled temperature (68° F.-72° F.), light (12-h light-dark cycle), and humidity (45-55%). The animals were allowed free access to water and food during the experiment.

Example 8

Identification of Compounds that Inhibit Kinases

The ability of Compound 10-2 [as shown in Example 3] was evaluated for its ability to inhibit certain oncogenic kinases. Cells were treated with compound 10-2 for 6 hours prior to addition of EGF to the growth medium for 15 minutes. Western blot analysis was performed to determine levels of the phosphorylated forms of EGFR, c-Met and Her2 receptor tyrosine kinases. It was found that incubation of cells with compounds of the present invention blocked activation of EGFR, c-Met and Her2 (see FIG. 1).

Figure 2:
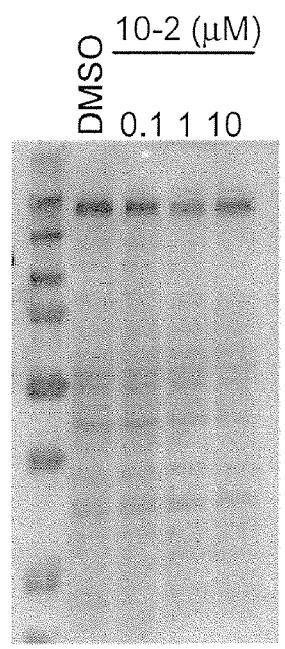
FIG. 2 shows that compound 10-2 inhibits activation of EGRF, cMet, and Her2, but does not cause a global reduction in tyrosine kinase activity.

Compound 10-2 [as shown in Example 3] was tested to determine whether it causes a global inhibition of tyrosine kinase activity. Compound 10-2 was treated in cells for 6 hours to examine its effect on levels of tyrosine phosphorylated proteins. A slight decrease was observed in total tyrosine phosphorylation in cells treated with greater than 1 µM 10-2. However, no decrease was observed in levels of phospho-tyrosine in cells treated with less than 1 µM 10-2 (see FIG. 2). These data suggest that Compound 10-2 specifically inhibits activation of EGFR, cMet, Her2, and possibly additional kinases, but does not cause a global reduction in tyrosine kinase activity.

Figure 3:
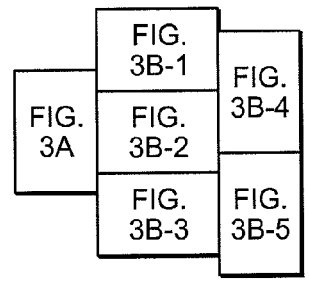
FIG. 3 shows the kinome profiles of the compound 10-2 and the control TKI.
Figure 3A:
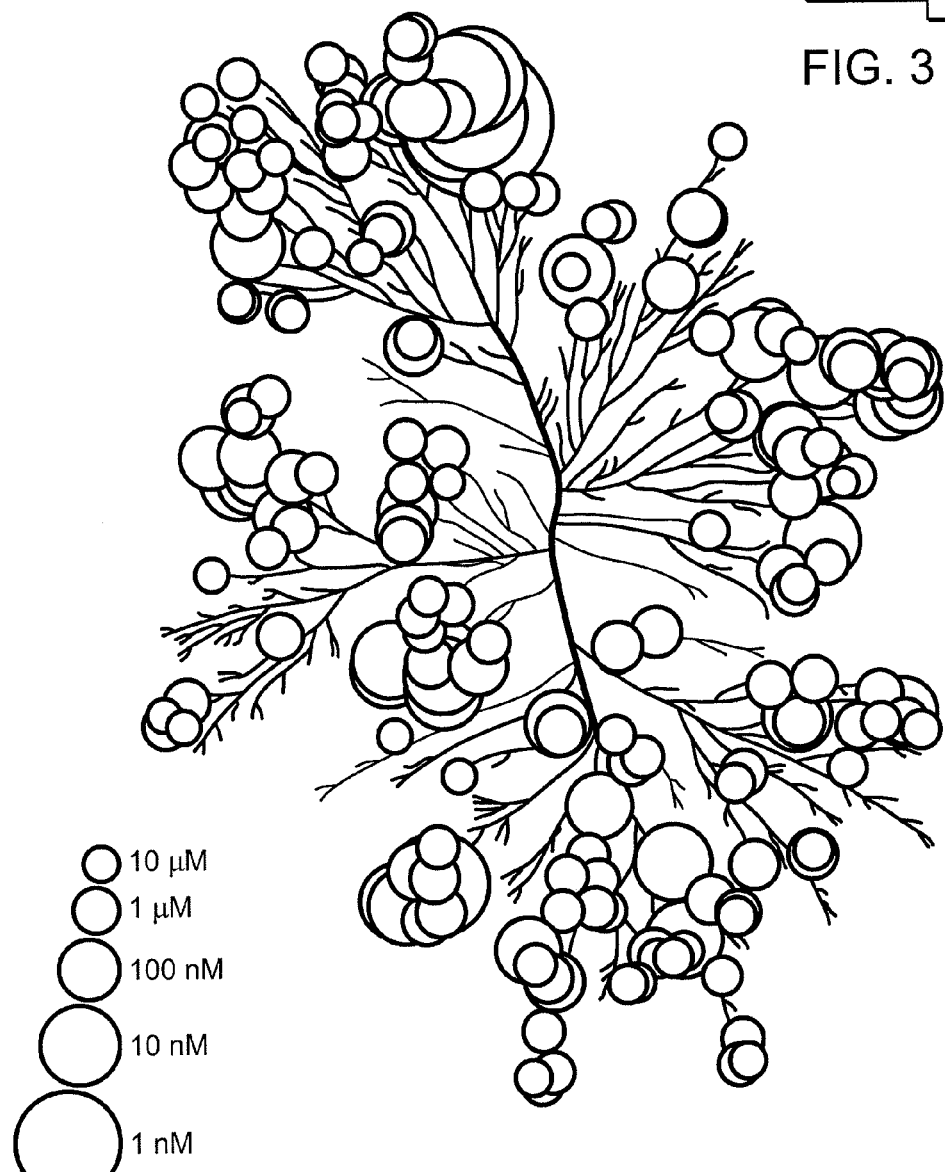
Figures 1, 3B:
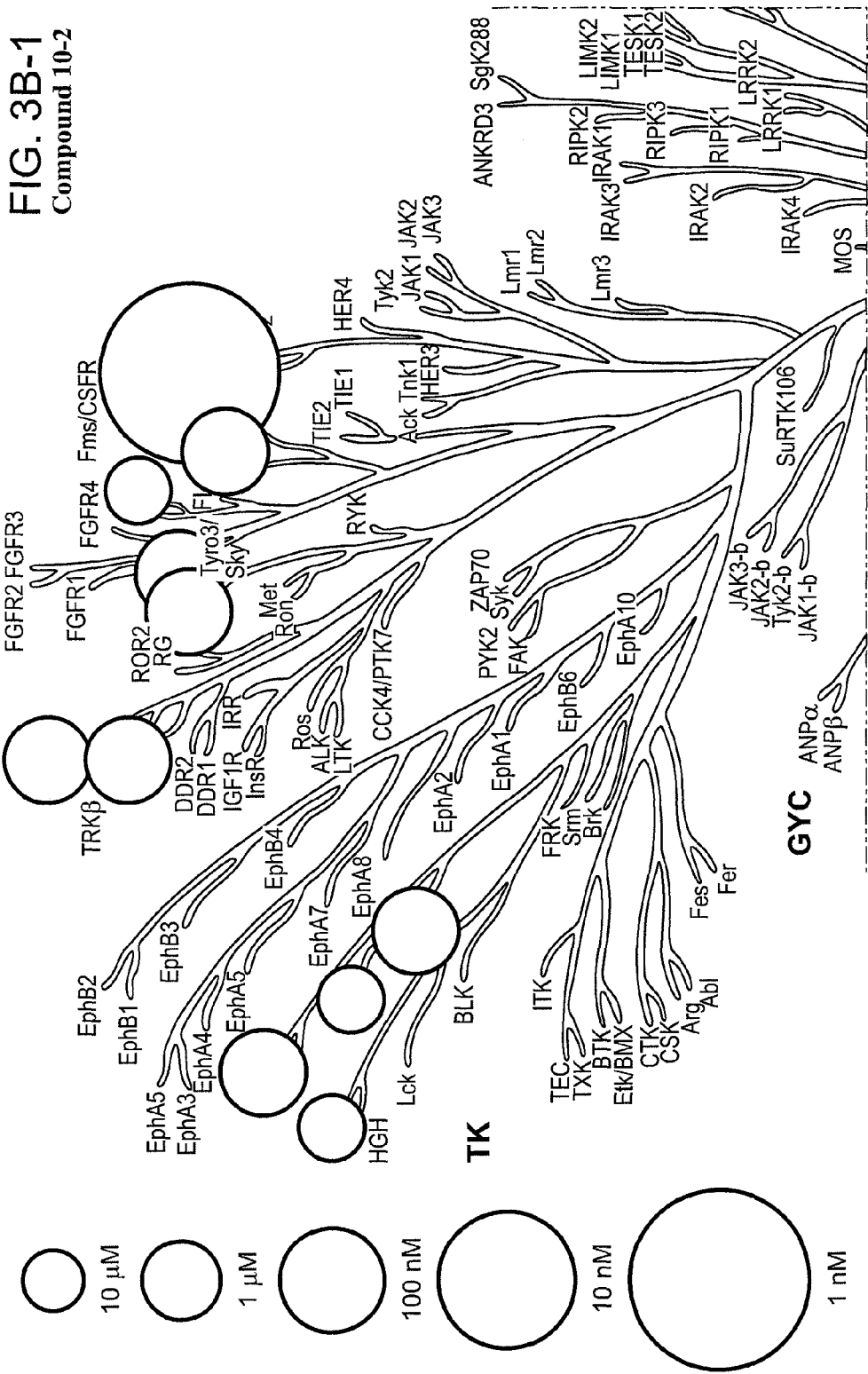
Figures 2, 3B:
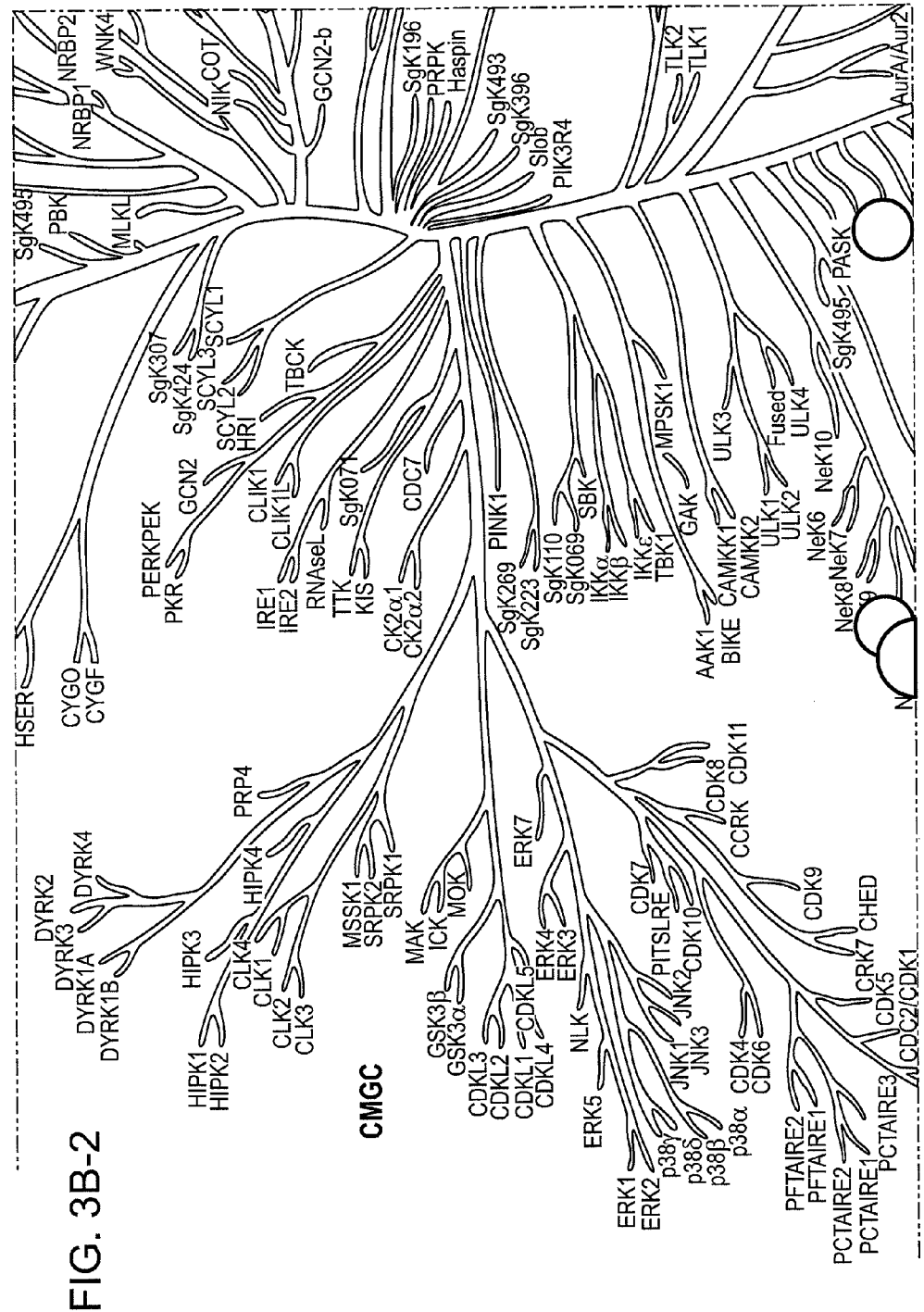
Figures 3, 3B:
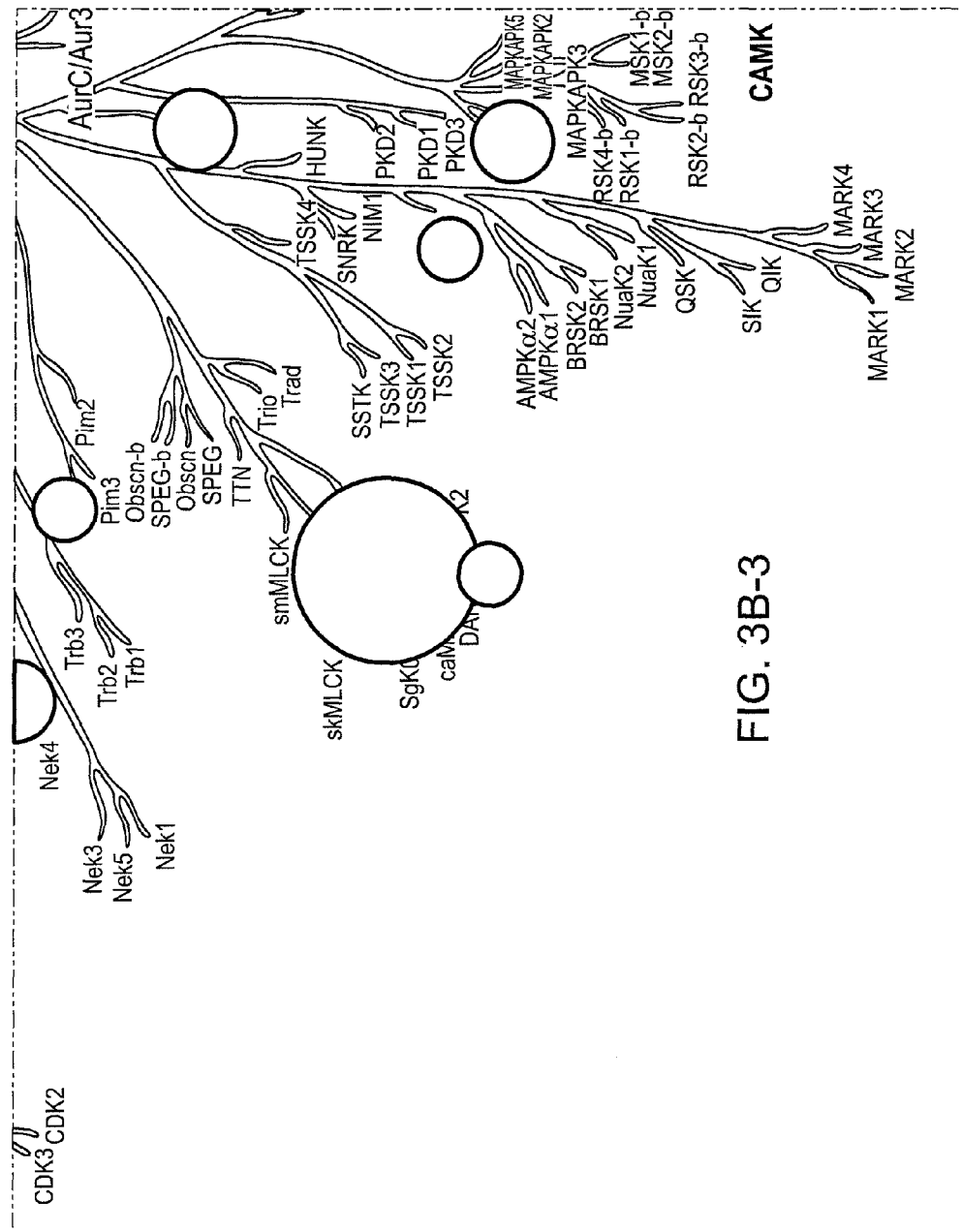

A kinase profile experiment was performed to determine the $IC_{50}$ of compound 10-2 for a panel of about 200 kinases. Compound 10-2 [as shown in Example 3] was found to selectively inhibit PDGFRα with an IC50 ranging from 4-30 nM, which is about 1000 folds selective over PDGFR beta. The kinome profile of compound 10-2 is compared to that of the reference compound served here as a control tyrosine kinase inhibitor (TKI). As you can see in FIG. 3, compound 10-2 has a much cleaner kinome profile, which suggests that compound 10-2 will have an improved toxicity profile than the reference compound.

Example 9

In vitro Cell Death Induction

Compounds 5 [as shown in Example 1], 3 [as shown in Example 1], 7-1 [as shown in Example 1], 10-2 [as shown in Example 3], 10-1 [as shown in Example 2], and 13-1 [as shown in Example 4] were tested for their ability to inhibit cell growth and promote cell death using the colony formation assay (CFA). Cells were treated for either 6 or twenty-four hours with the indicated compounds, and then allowed to grow for an additional 7-10 days. Cells were then stained, and colonies counted to determine IC-50 values. For purposes of illustrating only, the biological results of Compounds 5, 3, 7-1, 10-2, 10-1, and 13-1 are shown in Table 2.

TABLE 2

| Compounds | HT29 ($IC_{50}$) | MDA-MB-231 ($IC_{50}$) | FaDu ($IC_{50}$) |
|---|---|---|---|
| 5 | 10-25 µM | 6-10 µM | |
| 3 | 50-300 µM | 50-300 µM | |
| 7-1 | 6-10 µM | 6-10 µM | |
| 10-2 | 100-250 nM | 100-250 nM | |
| 10-1 | 1.5-3 µM | 0.8-1.5 µM | |
| 13-1 | 400-800 nM | 100-250 nM | |
| 13-2 | | | 300-400 nM |

Similarly, Compound 10-2 [as shown in Example 3] was tested against a wide range of cancer cell lines. The results show that Compound 10-2 has potent activities against these cells (Table 3).

TABLE 3

| Cell line | Tissue type | Compound 10-2 (µM) 6 hrs | 24 hrs |
|---|---|---|---|
| Dld1 | Colon cancer | 0.507 | 0.497 |
| SW480 | | 0.419 | 0.400 |
| HT29 | | 0.193 | 0.238 |
| H1299 | Lung cancer | 1.048 | 0.450 |
| A549 | | 0.509 | 0.502 |
| A431 | Skin cancer | 0.537 | 0.424 |
| HepG2 | Liver cancer | 0.907 | 0.386 |
| ACHN | Kidney cancer | 0.53 | 0.40 |
| FaDu | Head and neck cancer | 0.62 | 0.50 |

Example 10

Identification of Compound 10-2 that Target Cancer Stem Cells

Figures 3, 3B, 4:
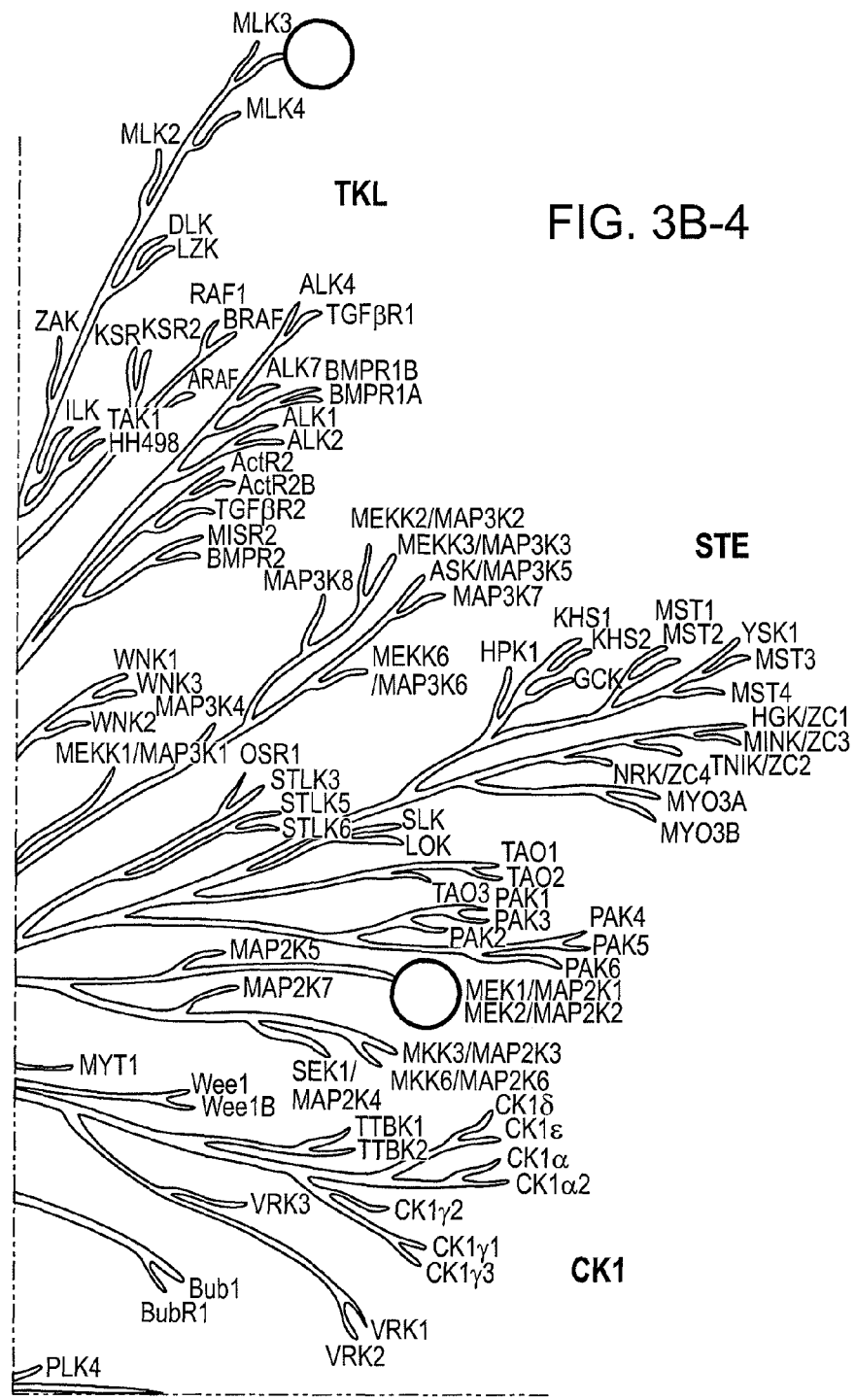
Figures 3, 3B, 4, 5:
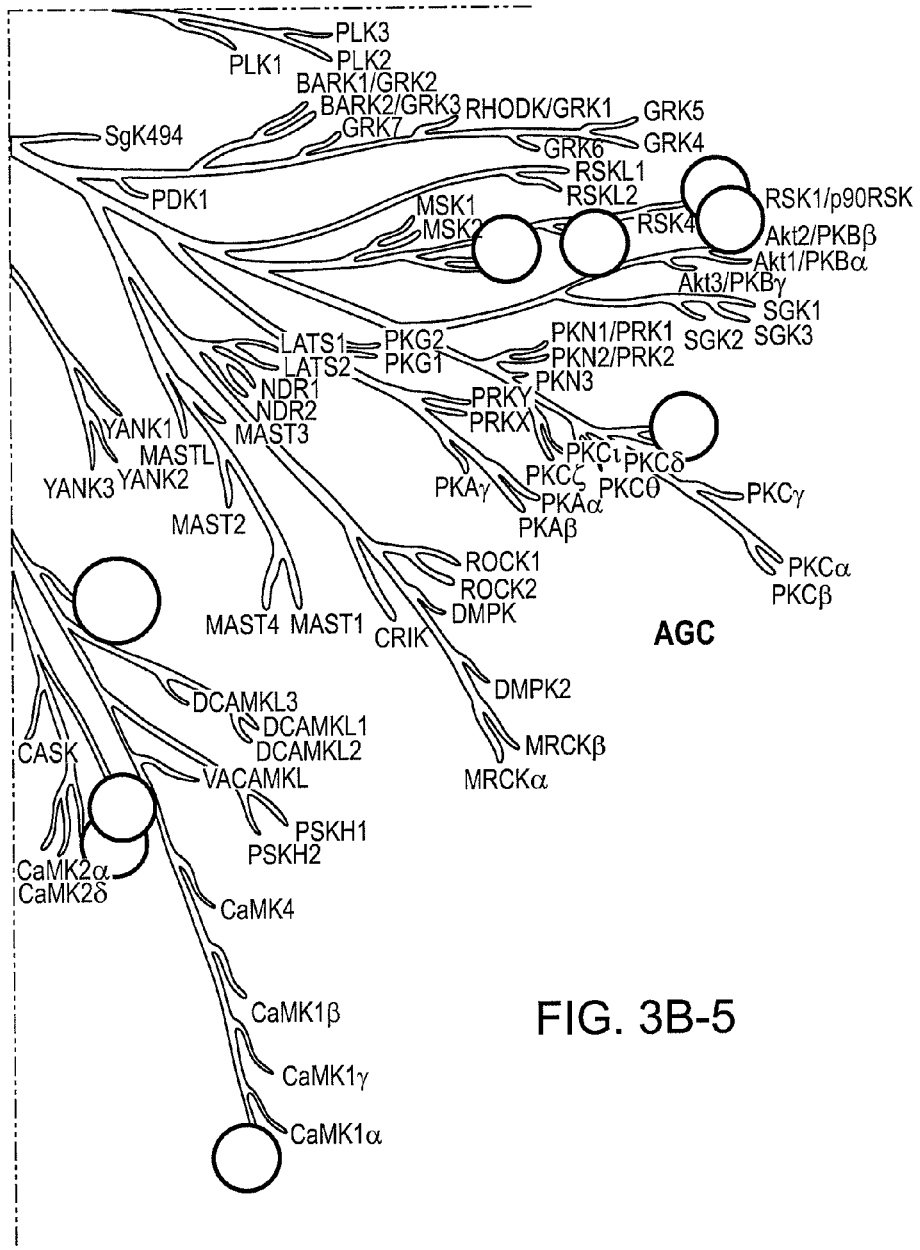
FIG. 5 shows that compound 10-2 inhibits CSC spherogenesis in vitro.

SW480 cells were stained with Hoechst. The side population (shown in FIG. 4A, upper left panel gated area) was sorted out to enrich the cancer stem cells. A control set of SW480 cells were first treated with Verapamil, an inhibitor of ABC transporters, before stained with Hoechst. As shown in the lower left panel of FIG. 4A, Verapamil treatment results in the loss of the side population. The SP represented 1.3% of parent population, and upon being cultured for seven days the sorted SP cells diminished from 98.5% to 10.1% (FIG. 4A, upper right panel). These data demonstrate a defining characteristic of CSCs, the ability to divide asymmetrically and to self-renew.

The $IC_{50}$ of compound 10-2 against the Hoechst side population was accessed in colony formation assays and was compared to the $IC_{50}$ against the non-side population. As shown in FIG. 4B, the side population is 2 fold more sensitive as the non-side population to compound 10-2. In addition, the side population is more resistant than the non-side population to Doxorubicin. These data suggest that compound 10-2 kill cancer stem cells.

The Hoechst side population cells were treated with compound 10-2 and the mode of cell death was accessed by Annexin V (an early marker for apoptosis) staining. As shown in FIG. 4C, the dying cells are Annexin V positive, demonstrating that compound 10-2 is apoptotic to cancer stem cells.

Figure 5A:
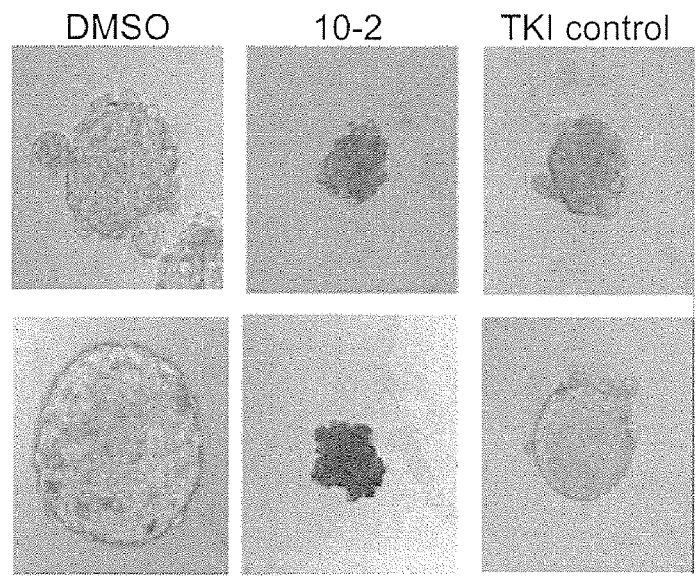
Figure 5B:
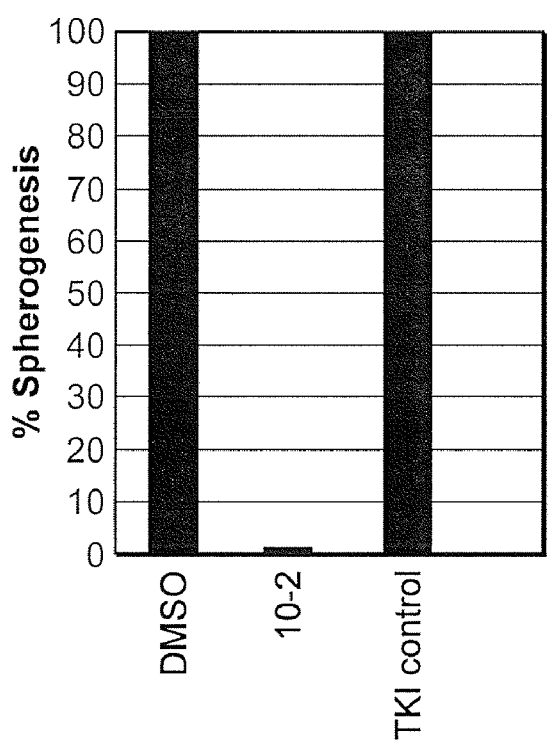

One of the hallmarks of cancer stem cells is their ability to self-renew. A reliable method of measuring the self-renewal capacity of cell populations is the ability to be cultured as spheres in the absence of serum or attachment. To determine the effect of compound 10-2 on CSC self-renewal, CSCs were isolated from FaDu human head and neck cancer cells by FACS using CSC surface marker CD44. Cells were cultured in the absence of attachment and serum for 5 days to form primary spheres. Primary spheres were then dissociated in Accumax to single cells, and were cultured as above for 72 hours before the addition of compound 10-2 or the control tyrosine kinase inhibitor (TKI). After five days of treatment, representative sphere images were captured before and after the addition of trypan blue to identify dead cells (FIG. 5A). Sphere growth was scored by counting the number of spheres possessing>50 cells. The % spherogenesis was calculated by setting the spherogenesis of the cells treated with DMSO as 100% (FIG. 5B). The results showed that compound 10-2, but not the control TKI, inhibits the CSC self-renewal.

Figure 6:
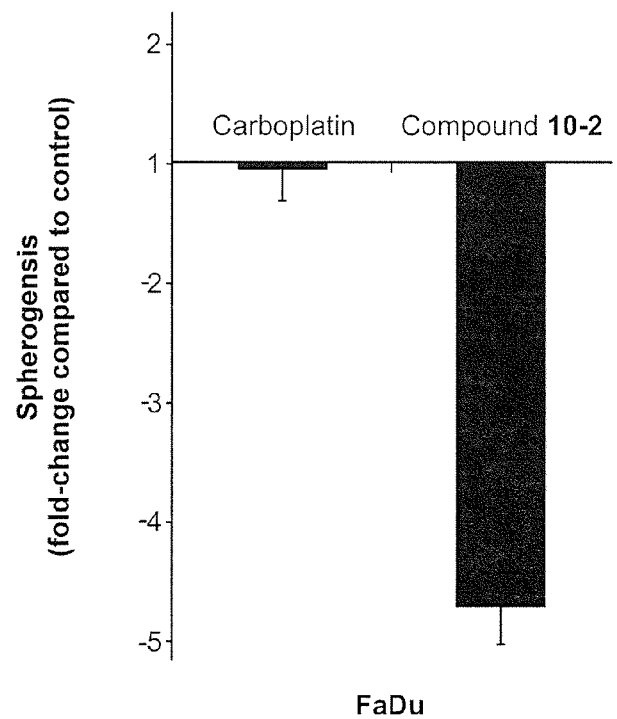
FIG. 6 shows that compound 10-2 inhibits CSC spherogenesis in vivo.

In addition, we also tested if compound 10-2 can target cancer stem cells in vivo. Six-week-old female athymic nu/nu mice were obtained from Charles River Labs (Wilmington, Mass.). Mice were injected subcutaneously on the flank with $6\times10^6$ FaDu cancer cells in 0.2 mL of serum-free DMEM. After xenografts reached ~200 mm³ in size, animals bearing FaDu xenograft tumors were administered daily with either vehicle, carboplatin (30 mg/kg), or compound 10-2 (100 mg/kg) via po for four days before sacrifice. Tumors were then collected for FaDu cells. Single cell suspensions were obtained following animal sacrifice, and sterile removal of tumors. Briefly, tumors were minced with sterile scalpels into 0.1 mm³ pieces before being digested in 1 mg/mL collagenase/HBSS for 15-30 minutes with constant agitation. Following passage through a 40 µm mesh filter, RBCs, dead cells, and cell debris were removed by layering the cell suspension onto 1 mL of Histopaque and collecting interface layer after centrifugation at 1440×g for 30 minutes. Live cells were then counted and used to measure their ability to form spheres. Cells were distributed to ultra low attachment 96 well plates at a density of 100 cells per well in cancer stem cell media (DMEM/F12, B27 Neurobasal supplement, 20 ng/mL EGF, 10 ng/mL FGF, 4 µg/mL insulin, and 0.4% BSA). Fresh media was added every three days, and sphere formation was determined after 10-14 days in culture. Spheres with >50 cells were scored. At conclusion of experiment, trypan blue was added to identify dead cells. As shown in FIG. 6, standard chemotherapies carboplatin does not target cancer stem cells evidenced by the unchanged spherogenesis. In contrast, even with only a four-day treatment, compound 10-2 significantly decreased cancer stem cells evidenced by the decreased spherogenesis.

Since compound 10-2 is a kinase inhibitor, the capability of compound 10-2 to induce apoptosis and inhibit self-renewal in cancer stem cell suggests that kinases inhibited by compound 10-2 are important for CSC(CSCPKs).

Example 11

In vivo Anti-Tumor Efficacy

Figure 7:
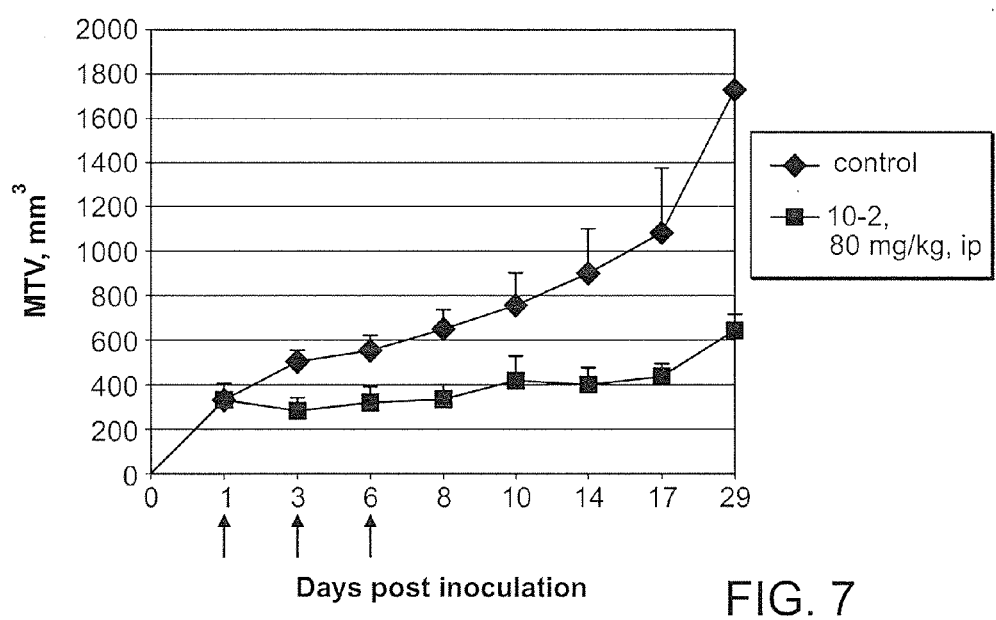
FIG. 7 shows that compound 10-2 exhibits antitumor activity in a human prostate cancer PC3 xenograft model.

The anti-tumor activity of compound 10-2 [as shown in Example 3] was tested in a xenograft mouse model. Immunosuppressed male mice with established subcutaneous PC3 human prostate cancer tumors were given compound 10-2 (80 mg/kg), or vehicle control intraperitoneal (ip.). Mice received a total of three treatments (as indicated as arrows in FIG. 7), and the Mean Tumor Volume (MTV) was analyzed. The vehicle control tumors grew comparably to that of previous studies performed with the PC3 model. As shown in FIG. 7, treatment with compound 10-2 caused significant suppression of tumor growth with a tumor growth inhibition (TGI) of 62.5% (p=0.02<0.05).

Figure 8:
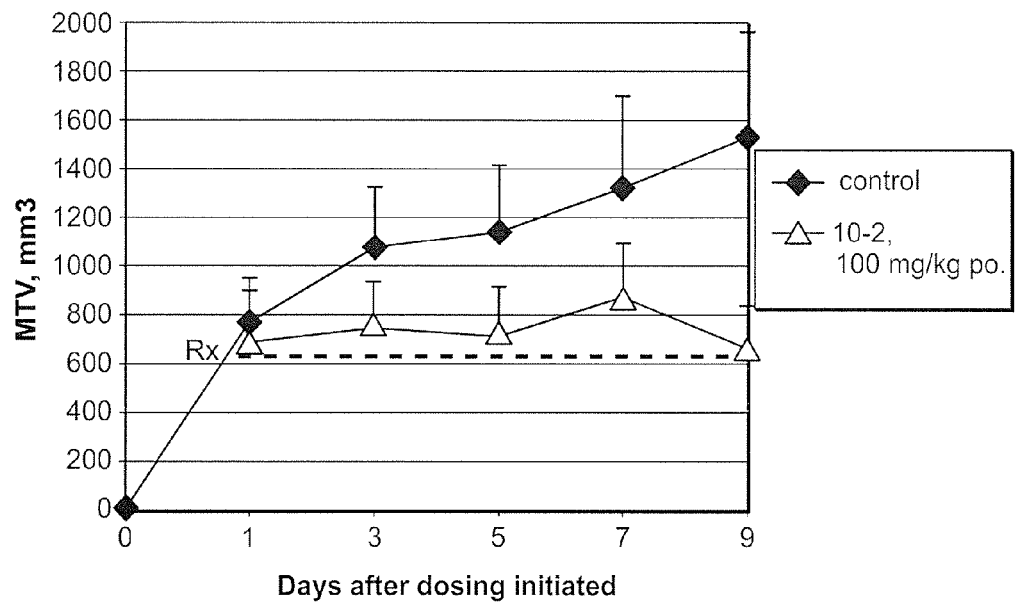
FIG. 8 shows that compound 10-2 exhibits antitumor activity in a human liver cancer HepG2 xenograft model.
Figure 9:
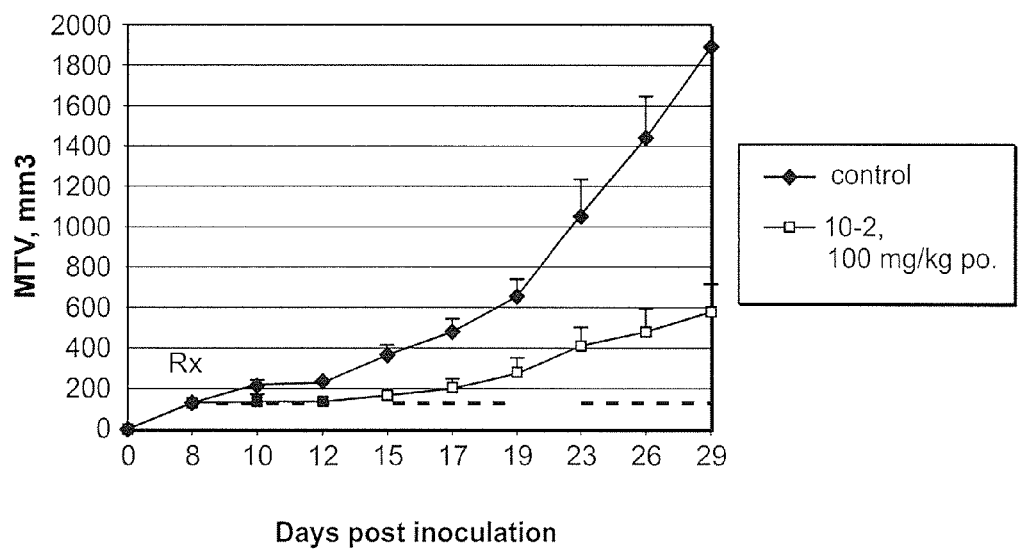
FIG. 9 shows that compound 10-2 exhibits antitumor activity in a human head and neck cancer FaDu xenograft model.
Figure 10:
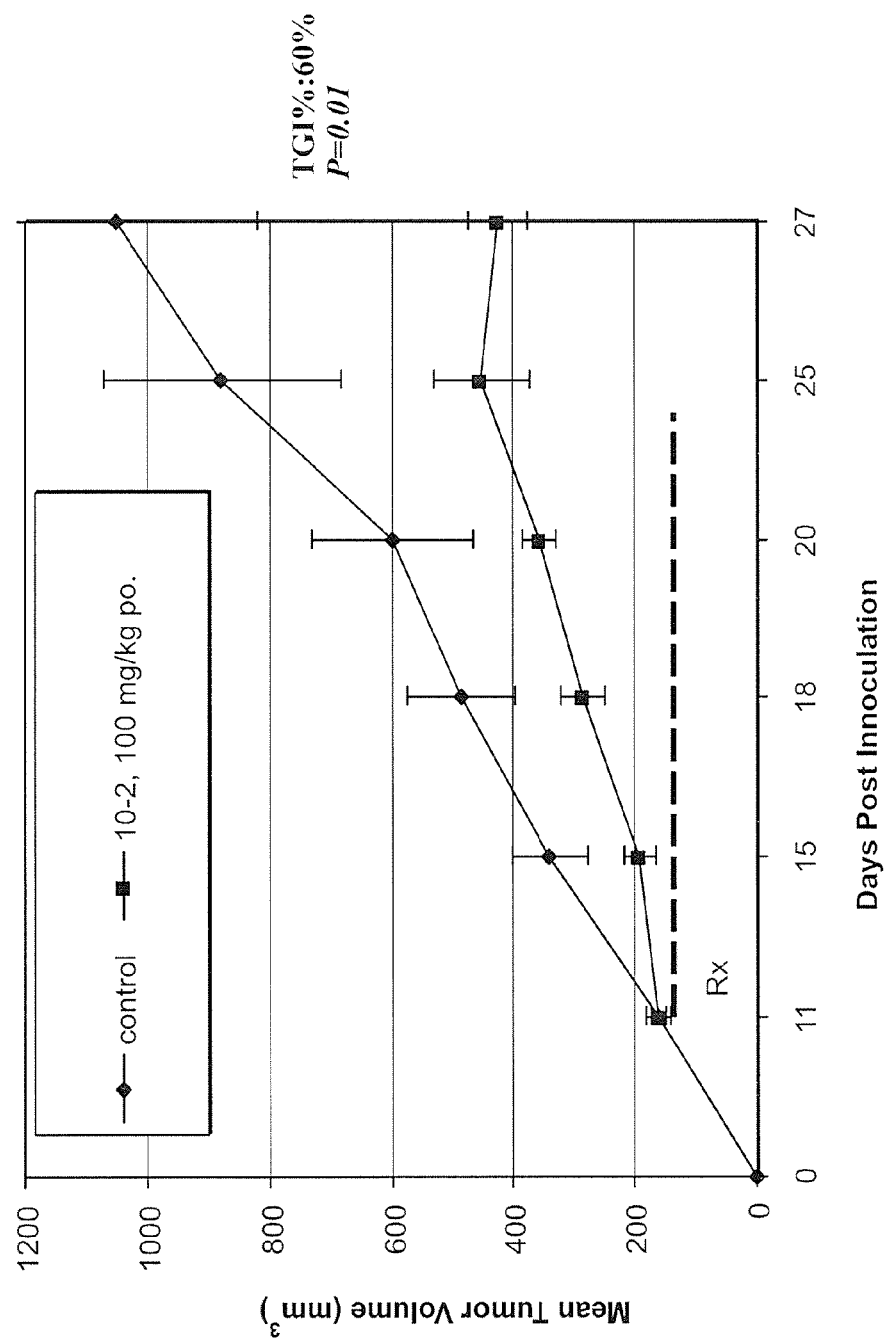
FIG. 10 shows that compound 10-2 exhibits antitumor activity in a human gastric cancer MKN45 xenograft model.

Similarly, anti-tumor activity of compound 10-2 [as shown in Example 3] was tested in human liver cancer HepG2 xenograft model (FIG. 8), human head and neck cancer FaDu xenograft model (FIG. 9), and human gastric cancer MKN45 xenograft model (FIG. 10). Compound 10-2 was administrated orally daily at 100 mg/kg in these three models for a period of time as indicated in the figures. Our data shows that compound 10-2 also potently inhibits the tumor growth in these two xenograft models.

REFERENCES

1. Pyle, A. D., L. F. Lock, and P. J. Donovan, *Neurotrophins mediate human embryonic stem cell survival*. Nat Biotechnol, 2006. 24(3): p. 344-50.
2. Betsholtz, C., *Role of platelet-derived growth factors in mouse development*. Int J Dev Biol, 1995. 39(5): p. 817-25.
3. Chott, A., et al., *Tyrosine kinases expressed in vivo by human prostate cancer bone marrow metastases and loss of the type 1 insulin-like growth factor receptor*. Am J Pathol, 1999. 155(4): p. 1271-9.
4. Dabrow, M. B., et al., *The effects of platelet-derived growth factor and receptor on normal and neoplastic human ovarian surface epithelium*. Gynecol Oncol, 1998. 71(1): p. 29-37.
5. Cools, J., et al., *A tyrosine kinase created by fusion of the PDGFRA and FIP1L1 genes as a therapeutic target of imatinib in idiopathic hypereosinophilic syndrome*. N Engl J Med, 2003. 348(13): p. 1201-14.
6. Heinrich, M. C., et al., *PDGFRA activating mutations in gastrointestinal stromal tumors*. Science, 2003. 299(5607): p. 708-10.
7. Holtkamp, N., et al., *Mutation and expression of PDGFRA and KIT in malignant peripheral nerve sheath tumors, and its implications for imatinib sensitivity*. Carcinogenesis, 2006. 27(3): p. 664-71.
8. Jackson, E. L., et al., *PDGFR alpha-positive B cells are neural stem cells in the adult SVZ that form glioma-like growths in response to increased PDGF signaling*. Neuron, 2006. 51(2): p. 187-99.
9. Jechlinger, M., et al., *Autocrine PDGFR signaling promotes mammary cancer metastasis*. J Clin Invest, 2006. 116(6): p. 1561-70.
10. Ongkeko, W. M., et al., *Expression of protein tyrosine kinases in head and neck squamous cell carcinomas*. Am J Clin Pathol, 2005. 124(1): p. 71-6.
11. Stock, P., et al., *Platelet-derived growth factor receptor-alpha: a novel therapeutic target in human hepatocellular cancer*. Mol Cancer Ther, 2007. 6(7): p. 1932-41.
12. Sulzbacher, I., et al., *Expression of platelet-derived growth factor-AA is associated with tumor progression in osteosarcoma*. Mod Pathol, 2003. 16(1): p. 66-71.
13. Wilczynski, S. P., et al., *Expression and mutational analysis of tyrosine kinase receptors c-kit, PDGFRalpha, and PDGFRbeta in ovarian cancers*. Hum Pathol, 2005. 36(3): p. 242-9.
14. Zhang, T., et al., *Overexpression of platelet-derived growth factor receptor alpha in endothelial cells of hepatocellular carcinoma associated with high metastatic potential*. Clin Cancer Res, 2005. 11(24 Pt 1): p. 8557-63.
15. Westermark, B. and C. H. Heldin, *Platelet-derived growth factor. Structure, function and implications in normal and malignant cell growth*. Acta Oncol, 1993. 32(2): p. 101-5.
16. Dolloff, N. G., et al., *Bone-metastatic potential of human prostate cancer cells correlates with Akt/PKB activation by alpha platelet-derived growth factor receptor*. Oncogene, 2005. 24(45): p. 6848-54.
17. Dolloff, N. G., et al., *Human bone marrow activates the Akt pathway in metastatic prostate cells through transactivation of the alpha-platelet-derived growth factor receptor*. Cancer Res, 2007. 67(2): p. 555-62.
18. Tsutsumi, N., et al., *Essential role of PDGFRalpha-p70S6K signaling in mesenchymal cells during therapeutic and tumor angiogenesis in vivo: role of PDGFRalpha during angiogenesis*. Circ Res, 2004. 94(9): p. 1186-94.
19. Joosten, P. H., et al., *Promoter haplotype combinations of the platelet-derived growth factor alpha-receptor gene predispose to human neural tube defects*. Nat Genet, 2001. 27(2): p. 215-7.
20. Lasky, J. A., et al., *Upregulation of the PDGF-alpha receptor precedes asbestos-induced lung fibrosis in rats*. Am J Respir Crit. Care Med, 1998. 157(5 Pt 1): p. 1652-7.
21. Ferns, G. A., et al., *Inhibition of neointimal smooth muscle accumulation after angioplasty by an antibody to PDGF*. Science, 1991. 253(5024): p. 1129-32.
22. Johnson, R. J., et al., *Inhibition of mesangial cell proliferation and matrix expansion in glomerulonephritis in the rat by antibody to platelet-derived growth factor*. J Exp Med, 1992. 175(5): p. 1413-6.
23. Raines, E. W., S. K. Dower, and R. Ross, *Interleukin-1 mitogenic activity for fibroblasts and smooth muscle cells is due to PDGF-AA*. Science, 1989. 243(4889): p. 393-6.
24. Ponti, D., et al., *Isolation and in vitro propagation of tumorigenic breast cancer cells with stem/progenitor cell properties*. Cancer Res, 2005. 65(13): p. 5506-11.

The invention claimed is:

1. A compound selected from the group consisting of:

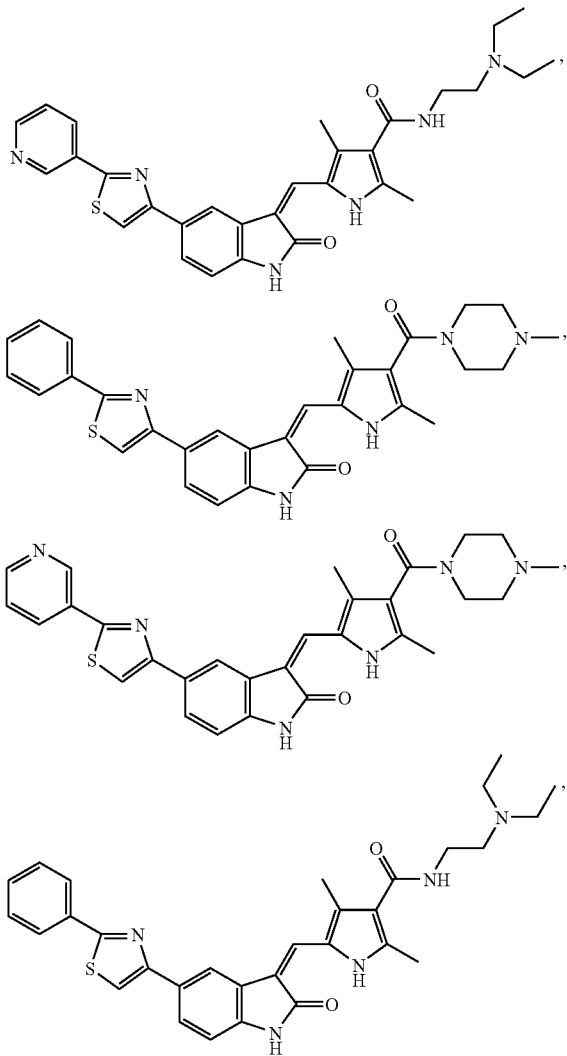

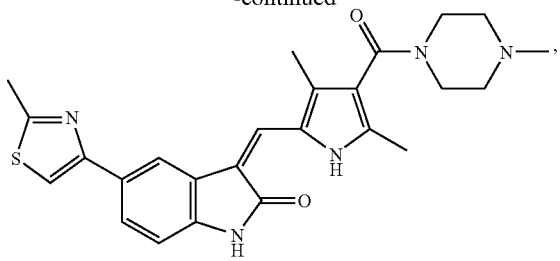
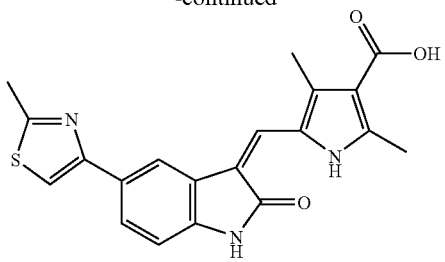

and an enantiomer, diastereomer, tautomer, or pharmaceutically acceptable salt or solvate thereof.

2. A pharmaceutical composition comprising a compound or a pharmaceutically-acceptable salt thereof as claimed in claim 1 and a pharmaceutically-acceptable excipient, carrier, or diluent.

3. The pharmaceutical composition of claim 2, wherein the pharmaceutically-acceptable excipient, carrier, or diluent is a solution mixture or a suspension mixture comprising, by weight, about 12.5% of dimethylacetamide, about 52.5% of PEG400, and about 35% of 20% Vitamin E.

4. The pharmaceutical composition of claim 2, further comprising at least one other anti-cancer therapy agent.

5. The pharmaceutical composition of claim 4, wherein said anti-cancer therapy agent is at least one agent selected from the group consisting of radiotherapy (XRT) agents, cytotoxic agents, targeted agents, and adjunctive agents.

6. The pharmaceutical composition of claim 4 or 5, wherein said anti-cancer therapy agent is selected from the group consisting of gemcitabine, erlotinib, paclitaxel, docetaxel, carboplatin, cisplatin, 5-fluorouracil, doxorubicin, sorafenib, imatinib, bevacizumab, cetuximab, and trastuzumab.

* * * * *